US010215683B2

(12) United States Patent
Deka

(10) Patent No.: US 10,215,683 B2
(45) Date of Patent: Feb. 26, 2019

(54) LIGHT SCATTER BASED APPARATUS AND METHODS FOR HEMATOLOGY ANALYSIS USING ONLY THREE DETECTORS

(71) Applicant: Chiranjit Deka, Morrisville, NC (US)

(72) Inventor: Chiranjit Deka, Morrisville, NC (US)

(73) Assignee: Chiranjit Deka, Morrisville, NC (US)

( * ) Notice: Subject to any disclaimer, the term of this patent is extended or adjusted under 35 U.S.C. 154(b) by 0 days.

(21) Appl. No.: 15/767,558

(22) PCT Filed: Nov. 2, 2015

(86) PCT No.: PCT/US2015/058629
§ 371 (c)(1),
(2) Date: Apr. 11, 2018

(87) PCT Pub. No.: WO2017/078672
PCT Pub. Date: May 11, 2017

(65) Prior Publication Data
US 2018/0299366 A1    Oct. 18, 2018

(51) Int. Cl.
*G01N 15/14*        (2006.01)
*G01N 35/10*        (2006.01)
*G01N 33/49*        (2006.01)
*G01N 33/50*        (2006.01)
*G01N 15/00*        (2006.01)

(52) U.S. Cl.
CPC ..... *G01N 15/1434* (2013.01); *G01N 15/1459* (2013.01); *G01N 33/49* (2013.01); *G01N 33/5002* (2013.01); *G01N 35/1095* (2013.01); *G01N 2015/0073* (2013.01)

(58) Field of Classification Search
CPC ........... G01N 15/1434; G01N 15/1549; G01N 2015/0073; G01N 33/49; G01N 35/1095; G01N 33/5002
See application file for complete search history.

(56) References Cited

U.S. PATENT DOCUMENTS 4,185,964 A    1/1980  Lancaster
4,284,412 A *  8/1981  Hansen .............. G01N 15/1459
                                              250/432 R
(Continued)

FOREIGN PATENT DOCUMENTS

WO    WO 2000/049385      8/2000

OTHER PUBLICATIONS

International Search Report and Written Opinion dated Mar. 31, 2016 in International Patent Application No. PCT/US2015/058629, filed Nov. 2, 2015.
(Continued)

*Primary Examiner* — Michael P LaPage
(74) *Attorney, Agent, or Firm* — Ward and Smith, P.A.

(57) ABSTRACT

Disclosed herein are apparatus, systems, and methods for optically identifying and enumerating cells present in a blood sample. A light scatter detector array may be used having no more than three light scatter detectors. The array may include a side scatter detector, an intermediate angle light scatter detector, and one of an axial light loss detector and a forward light scatter detector. A lytic reagent system is disclosed that allows for the identification and enumeration of five major leukocyte populations in normal whole blood on an instrument using no more than three light scatter detectors.

27 Claims, 29 Drawing Sheets

(56) References Cited

U.S. PATENT DOCUMENTS

| | | |
|---|---|---|
| 4,286,963 A | 9/1981 | Ledis et al. |
| 4,299,726 A | 11/1981 | Crews et al. |
| 4,485,175 A | 11/1984 | Ledis et al. |
| 4,599,307 A * | 7/1986 | Saunders ......... G01N 33/56972 250/461.2 |
| 5,125,737 A | 6/1992 | Rodriguez et al. |
| 5,155,044 A | 10/1992 | Ledis et al. |
| 5,510,267 A | 4/1996 | Marshall |
| 5,599,682 A | 2/1997 | Van Agthoven |
| 5,631,165 A | 5/1997 | Chupp et al. |
| 5,686,308 A | 11/1997 | Li et al. |
| 5,776,709 A | 7/1998 | Jackson et al. |
| 5,786,224 A | 7/1998 | Li et al. |
| 5,973,137 A | 10/1999 | Heath |
| 6,143,567 A | 11/2000 | Van Agthoven et al. |
| 6,228,652 B1 | 5/2001 | Rodriguez et al. |
| 6,232,125 B1 | 5/2001 | Deka et al. |
| 6,618,143 B2 | 9/2003 | Roche et al. |
| 6,869,798 B2 | 3/2005 | Crews et al. |
| 7,449,337 B2 | 11/2008 | Deka et al. |
| 7,611,849 B2 | 11/2009 | Hansen et al. |
| 2002/0115118 A1 | 8/2002 | Agthoven et al. |
| 2003/0025896 A1 | 2/2003 | Oever et al. |
| 2003/0030783 A1 | 2/2003 | Roche |
| 2006/0281143 A1* | 12/2006 | Liu ......... C12M 23/34 435/34 |
| 2007/0058252 A1* | 3/2007 | Fritz ......... G01N 15/1404 359/485.05 |
| 2008/0176331 A1* | 7/2008 | Deka ......... G01N 33/5094 436/17 |
| 2008/0187990 A1* | 8/2008 | Nagai ......... G01N 15/12 435/286.1 |
| 2010/0228491 A1 | 9/2010 | Gutierrez |
| 2011/0129864 A1 | 6/2011 | Beall et al. |
| 2012/0282600 A1 | 8/2012 | Wu et al. |
| 2012/0274925 A1 | 11/2012 | Chen et al. |
| 2012/0282598 A1 | 11/2012 | Wu et al. |
| 2012/0282599 A1 | 11/2012 | Wu et al. |
| 2016/0091484 A1* | 3/2016 | Yamada ......... G01N 15/1436 356/40 |

OTHER PUBLICATIONS

International Search Report and Written Opinion dated Oct. 1, 2014 in International Patent Application No. PCT/US2014/037508 filed May 9, 2014.

International Search Report and Written Opinion dated Nov. 6, 2017 in International Patent Application No. PCT/US2017/046961 filed Aug. 15, 2017.

George-Gay et al., "Understanding the Complete Blood Count with Differential," J. Perianesthesia Nursing, vol. 18, No. 2 Apr. 2003, pp. 96-117.

Supplementary European Search Report dated Oct. 20, 2016 in European National Phase Patent Application No. 14797140.2 filed May 9, 2014.

Kim et al., "Simultaneous differentiation and quantitation of erythroblasts and white blood cells on a high throughput clinical hematology analyzer" Clinical and Laboratory Hematology, John Wiley & Sons, Inc., Oxford, vol. 20, No. 1, Jan. 1, 1998, pp. 21-29.

Stewart et al., Resolving leukocytes using axial light loss, Cytometry, Alan Liss, New York, US, vol. 10, No. 4, Jul. 1, 1989, pp. 426-432.

Extended European Search Report dated Oct. 27, 2016 in European National Patent Application No. 14797140.2, filed May 9, 2014.

Preparation of Oral Proceedings dated Feb. 19, 2018 in European National Phase Patent Application No. 14797140.2 filed May 9, 2014.

* cited by examiner

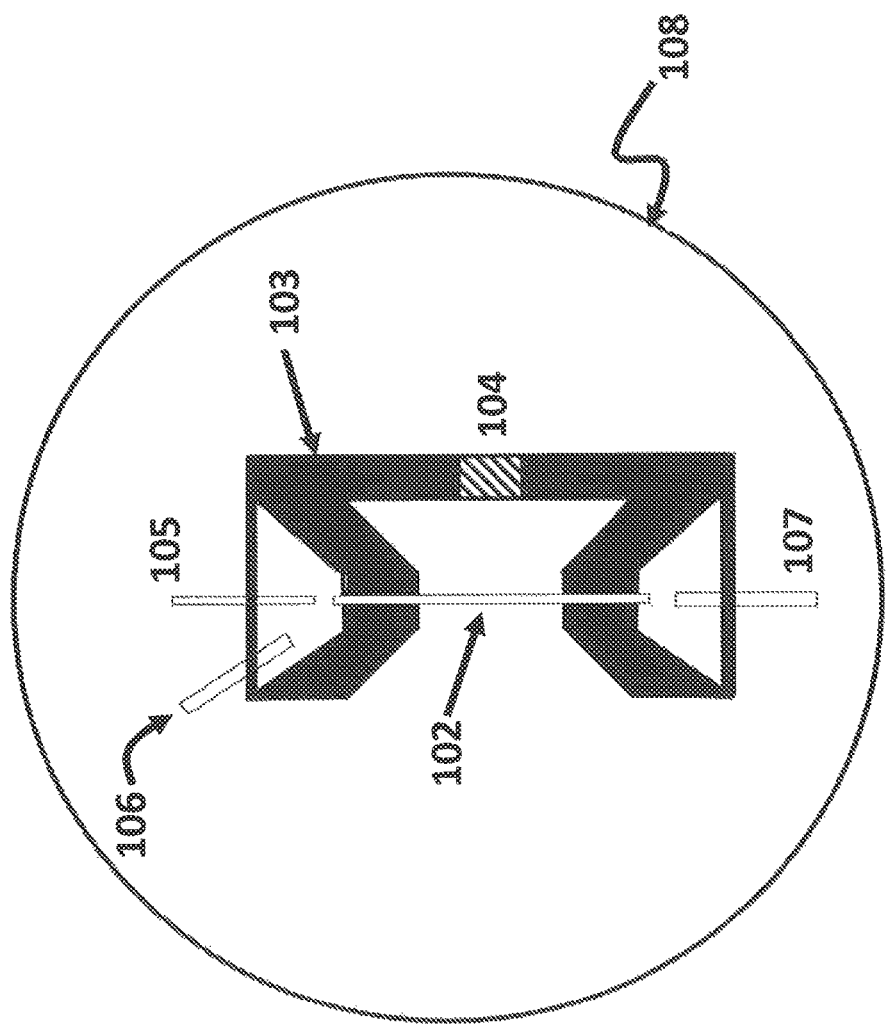

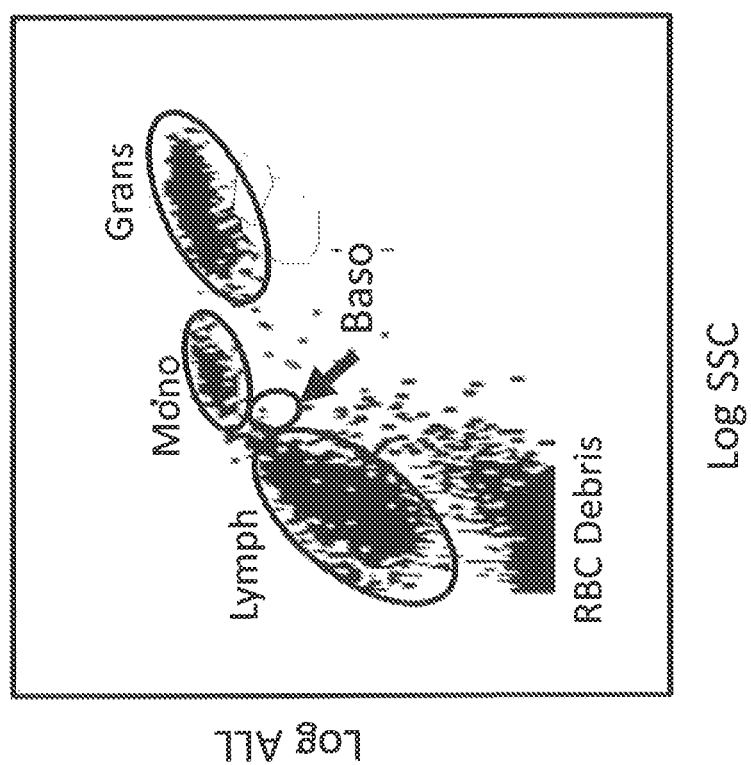

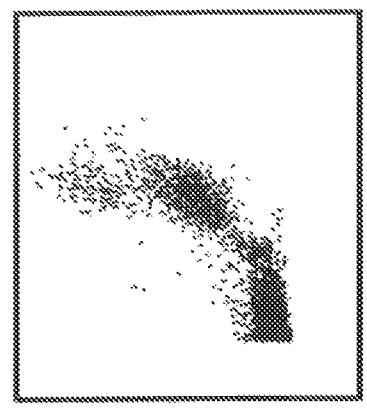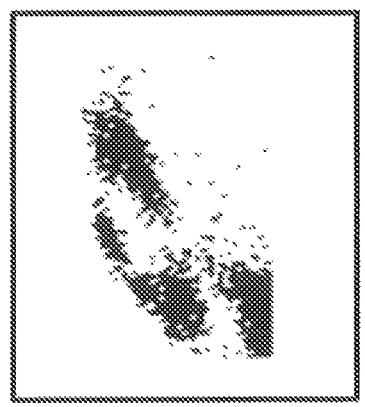
Fig. 13(b)

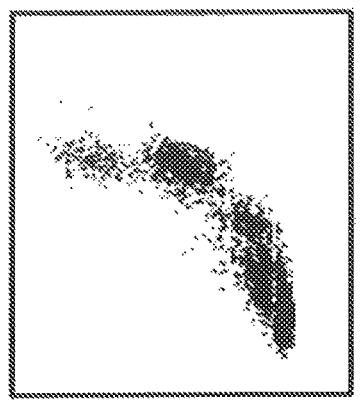
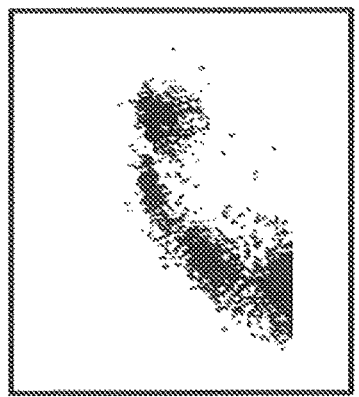
Fig. 13(c)

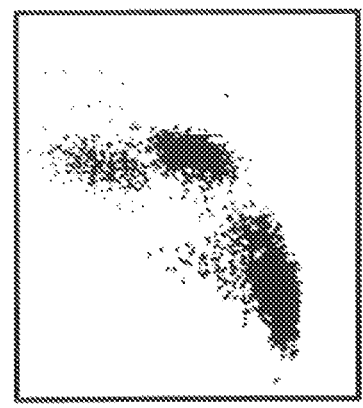
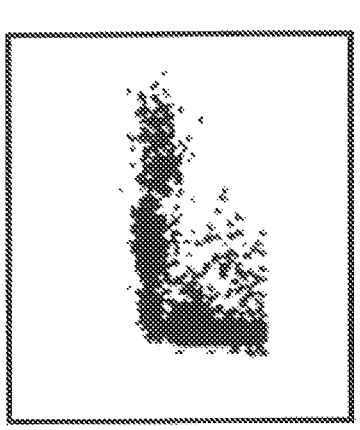
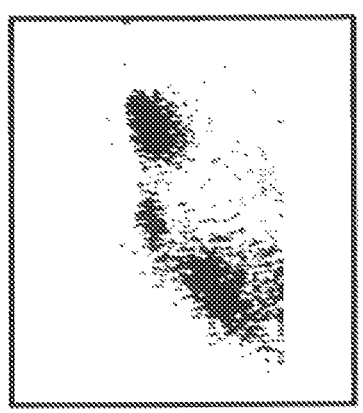
Fig. 13(d)

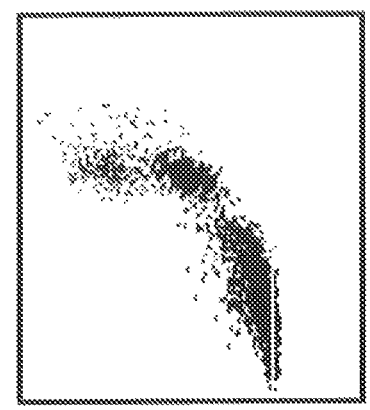
Fig. 13(e)

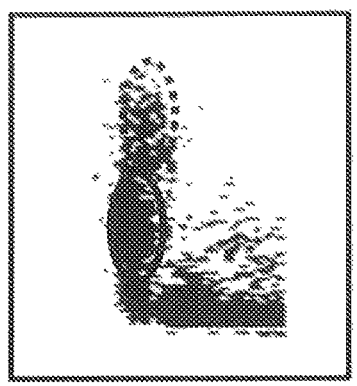 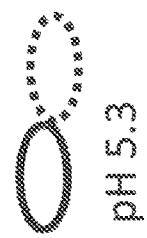 pH 5.3
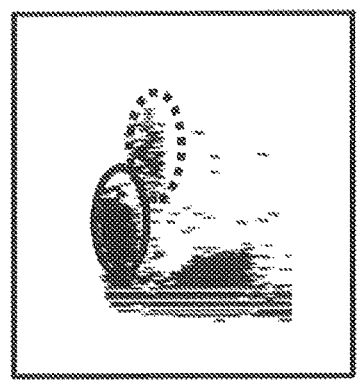 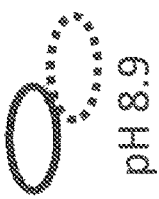 pH 8.9
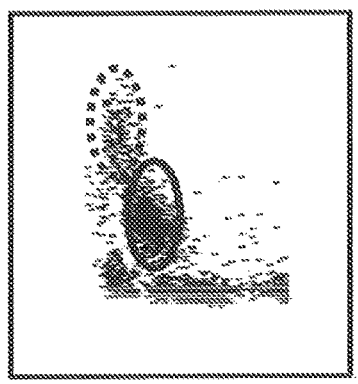 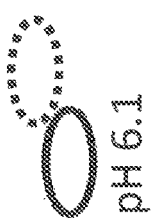 pH 6.1
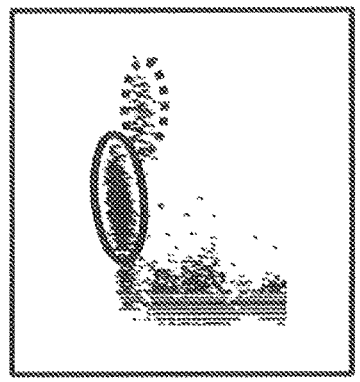 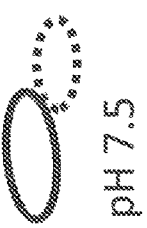 pH 7.5
Fig. 14

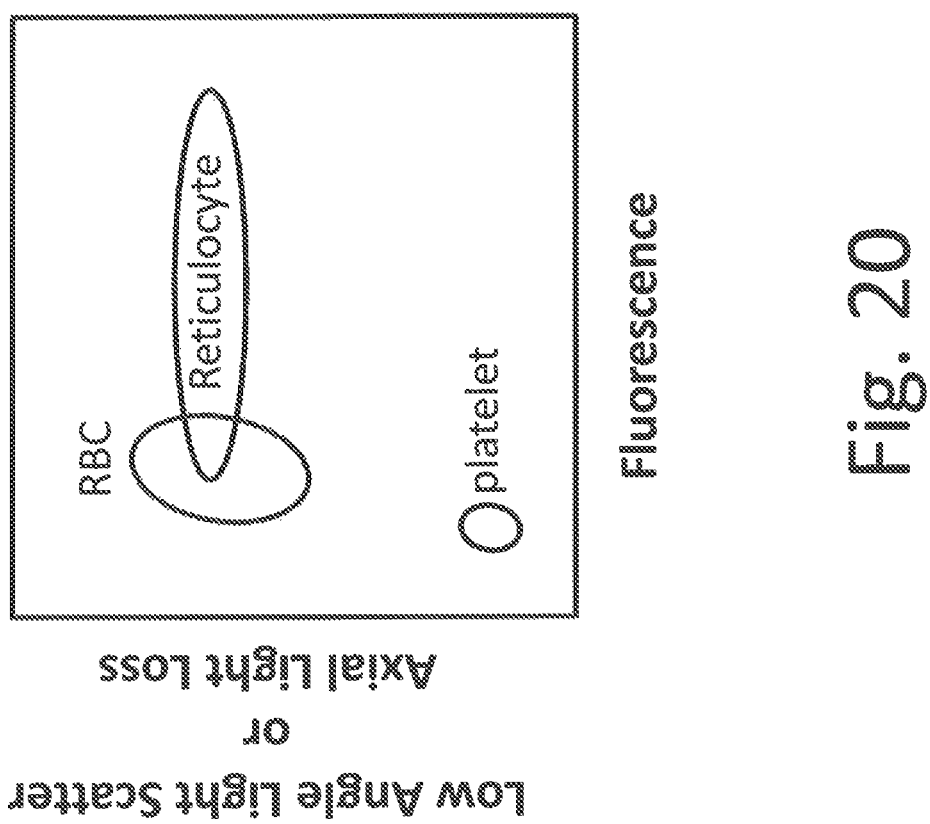

LIGHT SCATTER BASED APPARATUS AND METHODS FOR HEMATOLOGY ANALYSIS USING ONLY THREE DETECTORS

CROSS REFERENCE TO RELATED APPLICATIONS

This application is a U.S. National Stage of International Application No. PCT/US2015/058629, filed Nov. 2, 2015, the contents of these applications are incorporated by reference in their entirety.

INTRODUCTION

For routine hematology screening, automated cell counting by flow cytometry has all but replaced microscope based manual counting of cells on stained microscope slides. Over the last four decades, many new instruments, known as hematology analyzers, have appeared in the diagnostic market that perform such automated cell counting.

A key part of automated hematology analysis is the counting of white blood cells (or leukocytes) and the various subpopulations of leukocytes such as lymphocytes, neutrophils, monocytes, eosinophils etc. Leukocytes appear in normal blood in approximately 1:1000 ratio relative to the red blood cells. In order to count the leukocytes accurately in a hematology analyzer, it is customary to lyse the red blood cells in a manner that does not damage the leukocytes in the process. The key factors that determine the utility of such methods include effective lysis of the red blood cells to small fragments, fast lysis reaction, preserving the leukocytes from damage, enhancing the resolution between leukocyte subpopulations, and the ability to measure cells in both fresh and relatively old blood samples. Additional capabilities to perform immunochemical studies on cells exposed to the lytic reagent is highly desirable. Most importantly, technologies to enable all of these features in a low cost point-of-care device would be particularly beneficial.

The challenges associated in achieving the above goal are evident in the following discussion of existing patents related to hematology analyzers, lytic reagents, and integrated hematology and flow cytometry technologies.

U.S. Pat. No. 4,286,963 (to Ledis et al.) describes a lytic reagent and a method for achieving rapid hemolysis of erythrocytes in whole blood and automated analysis of lymphoid and myeloid subpopulations of leukocytes and the quantitative determination of hemoglobin. The lytic reagent is composed of a mixture of at least one quaternary ammonium surfactant and an aryl substituted short chain alkanol in buffered aqueous medium (pH 3.5 to 5.0). However, this reagent is limited in its ability to differentiate the leukocytes into two principal subpopulations: the lymphoid and myeloid fractions.

U.S. Pat. No. 4,485,175 (to Ledis et al.) describes a reagent system and method for performing differential determinations of leukocytes into three subpopulations utilizing automated cell counting equipment. This reagent system contains a blood diluent and a lytic reagent, comprising a mixture of quaternary ammonium surfactants. However, this reagent system limited its application to effect differentiation of the leukocytes into three subpopulations: lymphocytes, monocytes and granulocytes. Also, quaternary ammonium surfactants are strongly hemolytic and can cause lysis of the leukocytes. The differentiation, consequently, is based on the nuclear volumes of the leukocyte subpopulations. The application of these methods, alone or in combination with other means prohibits further refinement in the diagnostic process of various disease states based on the differences in the immunochemical response of the surface marker of the cell membrane.

U.S. Pat. No. 5,155,044 (to Ledis et al.) discloses a method and reagent system for the rapid isolation and analysis of leukocytes from a whole blood sample and enables automated differentiation into five subpopulations. The reagent system composed of an aqueous lytic reagent which comprises formic acid or a formic acid/acetic acid mixture, or a mixture of formic acid and saponin, and an aqueous salt quench solution to stop the lytic reaction. The amount of time of exposure of the blood sample to this lytic reagent system is critical to the differentiation method. This exposure period should not exceed ten seconds, and most preferably, requires only about six seconds or less, after which point a quenching reagent must be added to terminate the lytic reaction. The need for the quenching reagent renders the engineering system more complex and expensive. Also, the saponin used in the reagent system of U.S. Pat. No. 5,155,044 is a natural product and being a natural product, there is the potential of their being a finite source of saponin. In addition, the quality of the saponin can vary depending on its source.

Ledis et al. (U.S. Pat. No. 5,155,044) recognize that while many lytic agents and reagent systems can facilitate the differentiation of the leukocyte fraction of a blood sample (to a greater or lesser degree), each suffers from a common deficiency; namely, the inability to effect such differentiation without adversely altering the chemical balance of the cells which are subjected to such treatment. Where such alteration in the chemical balance is induced, the effect on the cellular population can range from relatively minor changes (i.e. swelling) to lysis. Dramatic chemical changes in the physiological environment of the leukocyte population also alter the immunochemical response of the leukocyte surface markers. The treatment of leukocytes with such traditional lytic agent system is, thus, inherently incompatible with further immunochemical study of these leukocytes. Such limitation prevented the use of lytic reagents, alone or in combination with other means, for further refinement in the diagnostic process of various disease states, based upon the differences in the immunochemical response of the respective surface markers of each such cell population.

Using the reagent system of U.S. Pat. No. 5,155,044 and a measurement system comprising electrical impedance (called DC), electrical conductivity (called RF) and light scatter detectors, Rodriguez (U.S. Pat. No. 5,125,737) was able to identify five leukocyte populations in normal blood. In one embodiment, using this reagent system that comprised a lytic reagent and a quench (or stop) reagent, the five populations of leukocytes were identified by either comparing the DC, RF and certain light scatter measurements over wide angles or comparing axial light loss and the light scatter intensity measured over a cumulative range of angles from 20-70 degrees. Rodriguez further demonstrated that in certain abnormal blood samples, a "small lymphocyte" population could be observed separately from the "normal lymphocytes" when viewed in the DC parameter. However, for normal samples only one lymphocyte population was observed. Furthermore, Rodriguez did not demonstrate the same observations on the abnormal samples when the measurements involved only light scatter detectors. The methods disclosed in this patent needed a quenching (or stop) reagent to stop the harsh lytic reaction from damaging the leukocytes. The requirement to use a quenching reagent renders the fluidic engineering design more complex, expensive and therefore undesirable in laboratories where cost is of critical concern, for example in resource limited settings. Furthermore, Rodriguez (U.S. Pat. No. 5,125,737) did not teach a method for identifying immunologically critical subpopulations of subpopulations in normal human blood by light scatter measurements, e.g., optic-only.

Yi Li (U.S. Pat. No. 5,686,308) teaches a lytic reagent for 5-part differential analysis of whole blood using DC, RF and light scatter measurement at 20-70 degree, where the reagent contained a long chain ethoxylated amine compound:

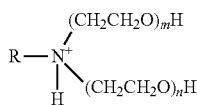

wherein R is an alkyl, alkenyl, or alkynyl group having 12-22 carbon atoms, m and n are each 1 or more, m+n is between 20 and 40, and acid to adjust the pH of the reagent to be within the range of 2.0 to 3.6. The reagent additionally contained an alkyl sulfate surfactant such as Sodium Dodecyl Sulfate (SDS).

Yi Li (U.S. Pat. No. 5,786,224) further discloses that in the above reagent, the presence of an ethoxylated amine compound is absolutely essential in order for it to work. A lytic solution containing 0.8 g/L SDS only or the SDS with acid but not including the polyoxyethylene based surfactant, caused significant leukocyte cell damage, especially the monocyte subpopulation which is almost completely destroyed. A practical limitation of this formulation was the requirement for the extremely long chain compounds, which are not readily available and are expensive to custom make.

In U.S. Pat. No. 6,232,125 Deka teaches a method that utilized DC and five different light scatter measurements to identify 5-part differential in whole blood. This method used the lytic reagent system of Yi Li (U.S. Pat. No. 5,686,308), including both a lytic reagent and a quenching reagent. The method teaches that basophils can be identified by measuring light scatter in four different angular ranges: 1.2°-3.3°, 4.6°-6.1°, 6.1°-7.7°, and 9.2°-11.0°, and using them in elaborate mathematical transformations. Eosinophils were obtained by comparing DC with a fifth light scatter detector 24°-35°. In addition to the drawbacks associated with the use of the lytic reagent system of U.S. Pat. No. 5,686,308, discussed above, Deka's method combining DC and multi-angle light scatter is expensive to build and not suitable for low-cost point-of-care applications.

Crews (U.S. Pat. No. 6,869,798) teaches a method for identification of five major populations of leukocytes of normal peripheral whole blood using axial light loss (also called Extinction) and three light scatter measurements at about 0°-30°, 30°-50°, and 50°-90° while using an alkaline (pH 9.1-10.7) lytic reagent in which the leukocytes were protected from damage by a leukopreservative agent selected from a group of certain short chain alkyl oxyethanol, such as 2-methoxyethanol, 2-ethoxyethanol, 2-propoxyethanol, or 2-isopropoxyethanol. Lymphocyte, granulocyte, monocyte and basophils were identified by comparing measurements at 0°-30° (forward scatter) and 30°-50° (called Wide Angle or WA). Eosinophils were identified by comparing axial light loss and the scattered light measured within the angles 50°-90° (called Super Wide Angle or SWA). The requirement for a detector to measure scattered light with a maximum angle of 90°, namely the SWA detector, is problematic if the system used for multi-part differential is also required to measure fluorescence, for example in a hybrid analyzer that combines automated white cell differential capabilities with fluorescence based cellular immunoassay requirements as the latter requires a wide angle 90° fluorescence light collection lens to collect the fluorescence light within a large cone around the 90-degree axis i.e., 50°-130° for high sensitivity. In such an example, the SWA detector would interfere with the fluorescence lens and significantly reduce the amount of fluorescence light that could be collected. Further, for this method to be integrated with a conventional flow cytometer that requires a conventional 90-degree light scatter detector, the system would then need a total of 5 light scatter detectors. In addition to such expensive disadvantages, Crews also did not teach an approach to identify subpopulation of any subpopulation in this method.

U.S. Pat. No. 5,510,267 (to Marshall) describes a flow cytometry lytic reagent and a method for providing a 5-part differential analysis of leukocytes. The method includes diluting a blood sample with a neutral and near isotonic diluent, mixing the diluted sample with the lytic reagent to lyse red blood cells, and analyzing the sample mixture in a flow cell by measuring 0°, 10°, 90° and 90° depolarized light scatter signals to differentiate leukocytes into the five major leukocyte subpopulations, namely neutrophils, lymphocytes, monocytes, eosinophils and basophils. Marshall teaches that the lytic reagent includes 2-phenoxyethanol which combines the function of leukoprotective and anti-microbial; Triton X-100 (octylphenoxypolyethoxyethanol) a lytic and wetting agent; and an organic buffer with pKa at or near 8.5 to maintain pH of the lysing reagent at 8.5. Furthermore, Marshall teaches the importance of pH to the function of the lytic reagent. More specifically, the optimal pH is 8.5, and with a lower range of 8.1 without significant effects on the reagent performance. However, if pH of the lytic reagent increases to 9.0, partial destruction of white blood cells can occur. In this patent, Marshal teaches that in order to resolve the eosinophils from the neutrophils, one needs two 90° detectors: (i) a photomultiplier tube (PMT) to collect 90° scattered light in polarization parallel to that of the laser beam and (ii) a second PMT with a cross-polarizing optical element in front of it in order to collect the 90° depolarized scattered light. The PMT based polarization/depolarization light scatter measurement system is expensive and not suitable for low-cost POC instruments. Further, Marshall did not teach an approach to identify any immunologically relevant subpopulation of any the major subpopulation of leukocytes in this method.

Deka and Feng (in U.S. Pat. No. 7,449,337) teach that for light scatter-based measurements, resolution between different leukocyte sub populations depends on a complex combination of size, internal structure, and relative refractive indices of the cellular material which may depend on the reagent to which the cells are exposed prior to measurement. As a result, whether or not a reagent system can enable accurate identification and analysis of individual leukocyte subpopulations after removal of the red blood cell (RBC) by lysis can only be determined by experimentation. In U.S. Pat. No. 7,449,337, Deka and Feng further teach a lytic reagent and a measurement method for the measurement of 4 populations of leukocytes, namely, eosinophil, neutrophil, lymphocyte and monocytes for canine whole blood, where the measurements comprised axial light loss and wide-angle 90-degree light scatter. The lytic reagent was maintained at the physiological pH of around 7.8, and comprised an anionic surfactant and an alkali metal salt to maintain the salt concentration between 15 and 150 mOsm. Deka did not teach that this reagent and measurement configuration could resolve the same four populations in human blood. Subsequent testing found that in fact axial light loss and wide angle 90-degree light scatter does not resolve eosinophils from the neutrophils in human blood.

In U.S. Pat. No. 6,618,143, Roche et al. teaches a high numerical aperture flow cytometer and method for differentiating eosinophils using a lens-less system in which a large photodiode is placed close to the flow cell to collect scattered light in a cone of at least 58° in the direction orthogonal to the laser beam. This patent teaches that a smaller cone of scattered light in the orthogonal direction fails to resolve eosinophils from the neutrophils. The high numerical aperture approach of U.S. Pat. No. 7,449,337 works for canine and feline blood, but generally fails to provide accurate eosinophil estimates in human blood. In order to collect at least a cone of 58° without a lens, a significant sized photodiode is required, which increases the capacitance of the detector and its noise, which in turn reduces resolution between neighboring cell populations. This is of particular problem when measuring human samples that have normal or low levels of eosinophils in the 1%-4% range. From a practical design perspective, there is additional disadvantage in that a large photodiode placed close to the flow cell, as required in this method, prevents the integration of this method with fluorescence based systems where fluorescence is required to be collected also in the orthogonal direction using high numerical aperture lens system. The photodiode prevents placement of such lenses due to mechanical interference. On the other hand, since the large surface of the light scatter photodiode also reflects a lot of spurious light into the opposite direction, it creates difficulty in placing fluorescence detectors in the opposite direction also.

As evident from the above discussion, conventional hematology analysis disclosures have numerous technological limitations related to the complexity of reagents and detection mechanisms. Many disclosures have attempted to combine a specific detection system with a specific set of reagent formulation and conditions. However, in doing so, these technologies have also become self-limiting in that they cannot be easily employed for applications beyond the conventional detection and enumeration of blood cells based on morphology, among other manners. A vast majority of such technologies are also unsuitable for implementation in low cost point of care applications because either they require many different types of disparate measurements (for example DC, RF and light scatter) or many different type of sensing within the same type of measurement (e.g., polarized and depolarized light scatter), or simply too many detectors of the same kind (e.g., 4 or greater number of light scatter detectors) for the simple requirement of obtaining the 4 major populations of leukocytes. None of these technologies permit analysis of cells based on immunophenotypes or detection of analytes in blood that are not attached to a cell, for example free antibodies or antigens. Such challenges will be more evident from the discussions provided in the following paragraphs on attempts made in integrating traditional hematology analysis methods with fluorescence flow cytometry, to derive additional data on abnormal cells from the same instrument, often labeled as "extended differential" analysis.

An "extended differential" or measurement of abnormal and immature cells, may be performed manually by first producing a blood-smear of a sample of interest on a glass microscope slide, staining the smear with a dye to enable the cells to be visualized, whereby abnormal or immature cells of interest can be visually differentiated from other cells, and then examining the resulting stained blood-smear under a micro-scope. Alternatively, some blood types of an extended differential measurement can be detected using a conventional flow cytometer. In such an instrument, a blood sample that has been previously prepared, e.g., by either (1) mixing the sample with fluorochrome-labeled monoclonal antibodies or the like which serve to selectively "tag" certain cells of interest, or (2) mixing the sample with a fluorescent stain adapted to selectively mark cells of interest, is passed through an optical flow cell. As each cell in the sample passes through the flow cell, it is irradiated with a beam of light adapted to excite the fluorescent material associated with the cells of interest. Fluorescent radiation emitted by each of the labeled cells, together with radiation scattered by each cell is detected and used to differentiate the cells of interest. Commercial, stand-alone, flow cytometers are made by Sysmex Corporation, Beckman Coulter, Life Technologies, Bio-Rad, and Becton Dickinson. It is known in the prior art to integrate individual flow cytometers and hematology instruments into a single automated laboratory system in which blood samples are automatically advanced along a track past these different instruments. As sample-containing vials pass each instrument, a blood sample is aspirated from each vial and analyzed by the instrument. Instrument systems combining discrete hematology and flow cytometry instruments are commercially available from Beckman Coulter and Sysmex Corporation.

In U.S. Pat. No. 5,631,165, an attempt is made to fully integrate the respective functions of hematology and flow cytometry instruments into a single instrument. Such an instrument comprises a plurality of transducers, including an optical flow cell adapted to make fluorescence and multi-angle light scatter measurements (including 4 detectors, two of which measure 90-degree polarized and depolarized light), an electrical impedance-measuring transducer (a Coulter transducer), and a colorimeter for measuring the overall hemoglobin content of a blood sample. The respective outputs from these transducers are processed and correlated to report on red, white and fluorescent cell. However, besides being complex and expensive, the requirement to correlate the respective outputs of multiple transducers in order to report certain characteristics of a cell type or subset can, under certain circumstances, be problematic in that it introduces an uncertainty in the analytical results. The validity of the requisite correlation step presupposes that the sample processed by one transducer is identical in content to that processed by the other transducer(s). This may not always be the case. Ideally, all of the measurements made on a cell should be made simultaneously by the same transducer. In such a case, there would be no need to correlate data from independent or separate transducers. Further, the simultaneous measurement of multiple parameters on a single cell using a single transducer enables a multidimensional cell analysis that would not be possible using separate transducers, or even using a single transducer when the parameter measurements are spatially separated in time.

Rodriguez (U.S. Pat. No. 6,228,652) discloses a blood analyzing instrument that includes a single transducer for simultaneously measuring the DC volume, RF conductivity, light scattering and fluorescence characteristics of blood cells passing through a cell-interrogation zone, where an electro-optical flow cell with a restricted cell-interrogation zone having a square transverse cross-section measuring approximately 50 um×50 um and length 60 um was used. The light scatter detector in this system comprised four detectors measuring scattered light in the ranges 10°-20°, 20°-70°, 10°-70°, and 80°-100°, which along with DC and RF comprise a total of six sensors for the hematology analysis. The basic 5-part differential hematology analysis method, including the internal design of the flow cell and the lytic reagents of this system are essentially the same as that disclosed in an earlier patent U.S. Pat. No. 5,125,737, except for a convex lens glued to one of its four exterior sides for collecting fluorescence. As a result, this system is subject to the same limitations and disadvantages associated with U.S. Pat. No. 5,125,737 as already discussed above. Most notably, the requirement to precisely drill a quartz or glass flow cell from both ends to within 60 µm of each other make it difficult to manufacture and therefore expensive. Additionally, the very narrow 50 µm×50 µm inner channel dimensions leave the flow cell susceptible to clogging when running blood.

Due to the use of many disparate measurements and sensors just to get the hematology 5-prt differential, the methods disclosed in U.S. Pat. Nos. 5,631,165 and 6,228,652 (among others) are complex and expensive, and are not suitable for use in low-cost applications, such as a point-of-care blood analyzer for use in resource limited settings.

Therefore, there is a need for improved instrument systems, reagents and analytical methods, that can perform leukocyte 5-part differential, platelet and RBC counts, and can be more easily and effectively implemented at relatively low-cost hematology analyzers and further, as needed, can also be more easily integrated and/or incorporated into a multifunction flow cytometry-based platform that is small, inexpensive and able to perform hematology, cellular immunophenotyping as well as non-cellular immunoassays.

Moreover, there is a need in the market for improved designs for morphology-based hematology analysis that can expand the analysis from the routine 5 major populations of leukocytes and delve deeper into subsets of those populations without having to use expensive antibodies or fluorescent dyes.

Significant challenges remain towards achieving the above goals, specifically:
(i) in minimizing the number and diversity of detection parameters to obtain a 5-part part differential;
(ii) in creating robust reagent systems that utilize readily available and inexpensive components in its formulation and yet operate under a wide range of conditions instead of just limited to highly acidic, highly basic or just physiological pH and allows 5-part differential using a small number of light scatter detectors; and,
(iii) making the hematology engineering configuration forward and backward compatible with conventional fluorescence flow cytometry so as to be able to affordably deliver multifunctionlity in a low cost instrument, preferably to the point-of-care market.

SUMMARY

In view of the above discussion, therefore, a primary object of this disclosure is to provide an apparatus capable of identifying and enumerating at least five subpopulations of leukocytes, red blood cells and platelets using no more than 3 light scatter detectors.

Another object of this disclosure is to provide a lytic reagent system that allows one to identify and enumerate five major leukocyte populations in normal whole blood on an instrument using no more than 3 light scatter detectors.

Another object of this disclosure is to provide reagent systems that allows one to identify and enumerate biologically significant subpopulation of at least one of the major five major leukocyte populations without using antibodies or fluorescent dyes.

Another object of this disclosure is to provide a hematology analysis method that can be easily integrated with a fluorescence flow cytometer.

In accordance with an aspect of the disclosure, embodiments of an apparatus for the identifying and enumerating constituents of a blood sample may include:
(a) a flow cell with an optically transparent flow channel that allows focused flow of a suspension of cells and/or particles to flow through it;
(b) a first fluidic device for aspirating whole blood sample and delivering the sample to at least one reaction chamber;
(c) a second fluidic device for delivering sample fluid from the at least one reaction chamber to a flow cell whole blood sample, wherein the sample fluid comprises whole blood and at least one reagent;
(d) at least one source of electromagnetic radiation to illuminate a portion of the flow channel;
(e) no more than three light scatter detectors to convert radiation scattered by constituents of the sample fluid:
 1. one detector measures radiation scattered in a direction substantially orthogonal to the plane defined by the longitudinal axis of the flow channel and an axis parallel to the direction of propagation of the electromagnetic radiation (the "side scatter (SSC) detector");
 2. one detector selected from either a forward scatter detector (FSC) or an axial light loss detector (ALL), where the FSC detector is configured to measure scattered light at angles less than 3° relative to the axis parallel to the direction of propagation of the electromagnetic radiation (and the ALL detector measure a decrease in optical signal on a detector place directly in front of the electromagnetic radiation transmitted through the flow cell and detects electromagnetic radiation within a narrow angle of less than 0.5° relative to the axis parallel to the direction of propagation of the electromagnetic radiation; and
 3. one detector, that measures light scatter within an angular range between about 25° and 45° relative to the axis along the direction of propagation of the electromagnetic radiation (the "intermediate angle light scatter (IALS) detector");
(f) at least one reagent for lysing the red blood cells; and
(g) at least one reagent for diluting the whole blood sample without lysing the red blood cells.

Embodiments of the apparatus may be configured to perform one or more of the following methods or assays, among other methods or assays for identifying and enumerating constituents of a blood sample:
(a) a method for identifying eosinophils, neutrophils, lymphocytes, monocytes, and basophils by comparing signals from the three light scatter detectors;
(b) a method for identifying eosinophils by comparing the light scatter signals from the IALS detector and the SSC detector;
(c) a method for identifying eosinophils by comparing the light scatter signals from the IALS detector and the ALL detector;
(d) a method for identifying platelets and red blood cells by comparing the light scatter signals from the ALL detector and the SSC detector.

In accordance with another aspect of the present approach, embodiments of an apparatus for identifying and enumerating constituents of a blood sample may include:

(a) a single flow cell with an optically transparent flow channel that allows focused flow of a suspension of cells and/or particles to flow through it;
(b) a first fluidic device for aspirating whole blood sample and delivering the sample to at least one reaction chamber;
(c) a second fluidic device for delivering sample fluid from the at least one reaction chamber to a flow cell whole blood sample, wherein the sample fluid comprises whole blood and at least one reagent;
(d) at least one source of electromagnetic radiation to illuminate a portion of the flow channel;
(e) no more than three light scatter detectors to convert radiation scattered by constituents of the sample fluid:
  1. a side scatter detector;
  2. an intermediate angle light scatter detector; and
  3. an axial light loss detector, which is considered a light scatter detector for purposes of this disclosure;
(f) at least one reagent for lysing the red blood cells;
(g) at least one reagent for diluting the whole blood sample without lysing the red blood cells.

Embodiments of the apparatus may be configured to perform one or more of the following methods or assays, among other methods or assays for identifying and enumerating constituents of a blood sample:
(h) a method for identifying eosinophils, neutrophils, lymphocytes, monocytes, and basophils by comparing signals from the three light scatter detectors;
(i) a method for identifying eosinophils by comparing the light scatter signals from the IALS detector and the SSC detector;
(j) a method for identifying eosinophils by comparing the light scatter signals from the IALS detector and the ALL detector;
(k) a method for identifying platelets and red blood cells by comparing the light scatter signals from the ALL detector and the SSC detector.

In some embodiments, at least one subpopulation of at least one of the five major leukocyte populations are identified and enumerated by analyzing the combination of their respective light scattering properties as measured by the ALL, SSC and IALS detectors.

In some embodiments, subset of lymphocytes in normal human peripheral blood are differentiated by adding non-fluorescent reagent components that dramatically change the light scatter properties of specific subpopulations. In some embodiments, a reagent containing the salt of an alkaline earth metal (e.g., $MgCl_2$) can be used to differentiate the predominantly CD4 T-cells based on light scatter properties. In some embodiments, the relative ratio of alkali metal salt molar concentration to alkaline earth metal salt molar concentration may be about 4:1.

Some embodiments of the apparatus further include at least one fluorescence detector, in addition to the ALL, IALS, and SSC detectors.

Described herein are embodiments of an apparatus for optically identifying and enumerating cells present in a blood sample. Generally, identifying and enumerating cells can include the identification and enumeration of five subpopulations of leukocytes, and/or the identification and enumeration of erythrocytes and thrombocytes. In some embodiments, an apparatus for optically identifying and enumerating cells present in a blood sample may have an optical flow cell defining a flow channel, an energy source for emitting electromagnetic radiation in a first direction to illuminate a region of the flow channel, and a light scatter detector array having no more than three light scatter detectors. The light scatter detector array may have a side scatter detector, an intermediate angle light scatter detector, and either an axial light loss detector or a forward light scatter detector. Some embodiments may also a have fluorescence detector that detects fluorescent light emitted from the sample flowing through the flow channel.

In some embodiments, the side scatter detector measures light scatter around an axis substantially perpendicular to the electromagnetic radiation direction. The detection cone may be a cone of full angle less than 50° centered around the axis. In some embodiments, the detection cone may be a cone of full angle of about 30° centered around the axis.

In some embodiments, the intermediate angle light scatter detector detects light scattered at angles from about 25° to about 45° relative to the electromagnetic radiation direction. In some embodiments, the intermediate angle light scatter detects light scattered within a polar angle from about 35° to about 45° and an azimuthal angle between 0° and about 90°, relative to the electromagnetic radiation direction. In some embodiments, the intermediate angle light scatter detector is configured to detect light scattered within a polar angle from about 35° to about 45° and an azimuthal angle between 20° and about 50°, relative to the first direction. In some embodiments, the intermediate angle light scatter detector is configured to detect light scattered within a polar angle from about 35° to about 45° and an azimuthal angle between 30° and about 35°, relative to the first direction. In some embodiments, the intermediate angle light scatter detector is configured to detect light scattered within a polar angle from about 41° to about 45° and an azimuthal angle between 0° and about 90°, relative to the first direction. In some embodiments, the intermediate angle light scatter detector is configured to detect light scattered within a polar angle from about 41° to about 45° and an azimuthal angle between 20 and about 50°, relative to the first direction. In some embodiments, the intermediate angle light scatter detector is configured to detect light scattered within a polar angle from about 41° to about 45° and an azimuthal angle between 30° and about 35°, relative to the first direction. The intermediate angle light scatter in some embodiments may be configured to detect light scattered within a polar angle from about 41° to about 45° and an azimuthal angle between 0° and about 90°, relative to the electromagnetic radiation direction.

In some embodiments, the third detector may be an axial light loss detector, generally referred to in this disclosure as a light scatter detector. The axial light loss detector may be configured to measure electromagnetic radiation within an angle less than about 0.5° relative to the electromagnetic radiation direction. In other embodiments, the third detector may be a forward light scatter detector configured to measure light scattered at angles less than 3° but greater than about 0.5° relative to the electromagnetic radiation direction.

As described herein, embodiments of the three-detector apparatus may optically identifying and enumerating cells present in a blood sample because of the novel lytic reagents disclosed herein. For instance, in some embodiments the lytic reagent modifies the light scatter property of one or more subpopulations of leukocytes. Thus, some embodiments of the apparatus may include a container with a lytic reagent that lyses the red blood cells. In other embodiments, lysing may occur prior to introducing a sample to the apparatus. In some embodiments, the lytic reagent includes at least one alkaline earth metal salt. The alkaline earth metal salt(s) may include magnesium halide, calcium halide, barium halide, and beryllium halide. Methods for identifying and enumerating CD4 cells in a flow cytometer (which includes a hematology analyzer) may include mixing a blood sample with an embodiment of the reagent described herein. For example, the reagent may include at least one alkaline earth metal salt selected from the group consisting of magnesium halide, calcium halide, barium halide, and beryllium halide.

In some embodiments, the lytic reagent has a surfactant and an alkali metal salt. The alkali metal salt may be, for example, sodium halide and potassium halide. In some embodiments, the lytic reagent is maintained at pH of about 4.5 to about 8.9, and in some embodiments about 4.6 to about 8.0, and osmolality of the lytic reagent is between about 5 mOsm and about 150 mOsm. In some embodiments, the lytic reagent may have about 15 mM to about 30 mM of NaCl, sodium dodecyl sulfate at a concentration of about 0.001% w/v to about 0.005% w/v, and is at a pH of about 7.0 to about 7.5. Some embodiments of the lytic reagent include at least one alkaline earth metal salt, including, for example, magnesium halide, calcium halide, barium halide and beryllium halide. In some embodiments, the lytic reagent may include a surfactant and an alkali metal salt in a hypotonic solution. Some embodiments may have NaCl and $MgCl_2$ at a relative concentration ratio of about 4:1. In some embodiments, the lytic reagent has an alkaline earth metal salt, without an alkali metal salt.

Some embodiments of the apparatus may have a container with a non-lysing diluent. The diluent may have a non-ionic detergent, such as, for example, n-dodecyl-β-D-maltoside. In some embodiments, the concentration of n-dodecyl-β-D-maltoside may be adjusted to substantially sphere red blood cells when added to a whole blood sample. In some embodiments, the diluent may be a substantially isotonic solution.

Embodiments may be in the form of methods for optically identifying and enumerating cells present in a blood sample, using only three detectors. The method may include exposing at least one aliquot of the blood sample to at least one of a lytic reagent that lyses the red blood cells and a diluent that does not lyse the red blood cells; flowing a blood sample through a flow channel in an optical flow cell; focusing within the flow channel an electromagnetic radiation propagating in a first direction; detecting light scattered from cells flowing though the flow channel with a light scatter detector array having no more than three light scatter detectors.

The present approach and its many advantages will be better appreciated from the following description of embodiments and results of experiments conducted in the embodiments and the related drawings.

DRAWINGS

Figure 3B:
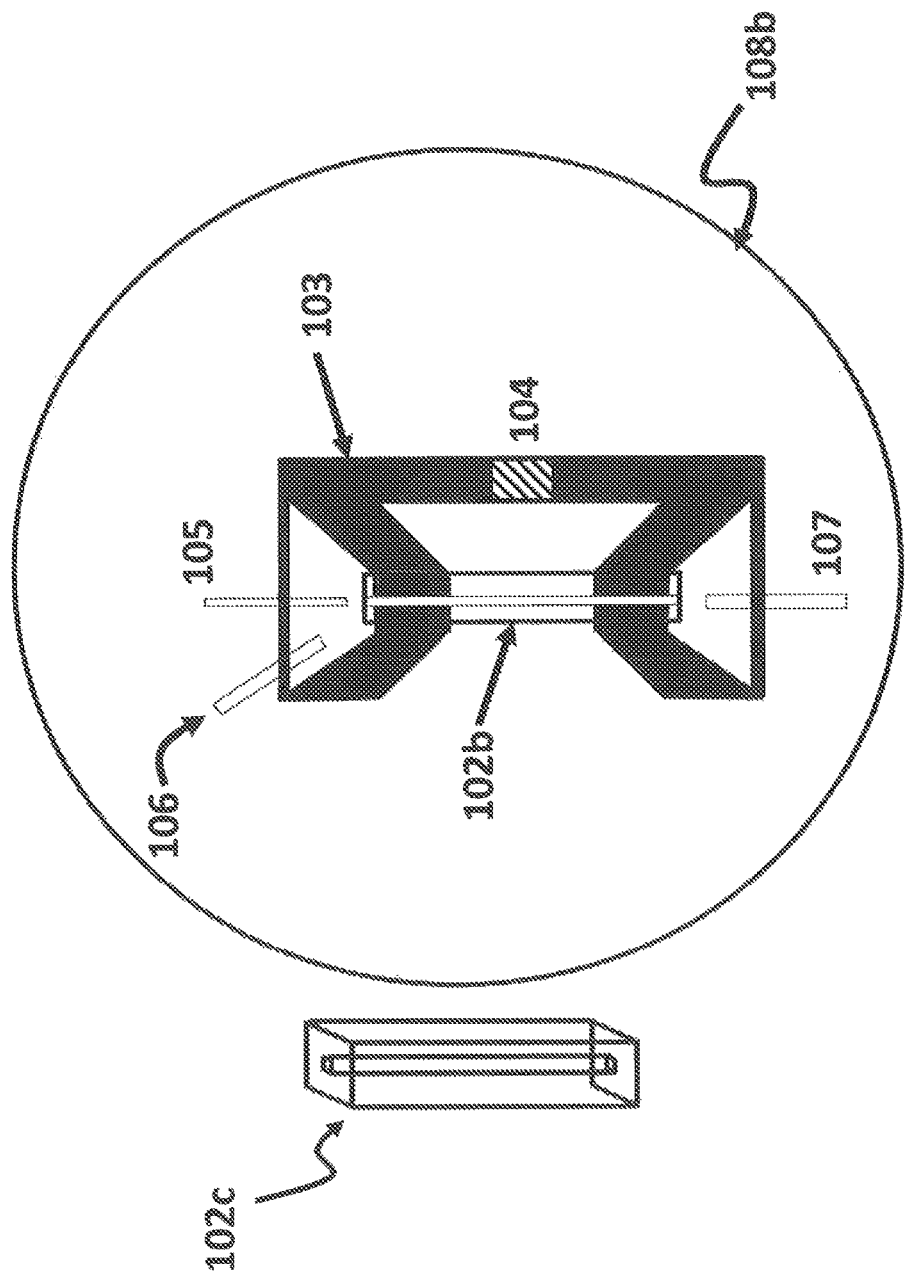

FIGS. 3(A) and 3(B) illustrate embodiments of a flow cell.

Figure 4:
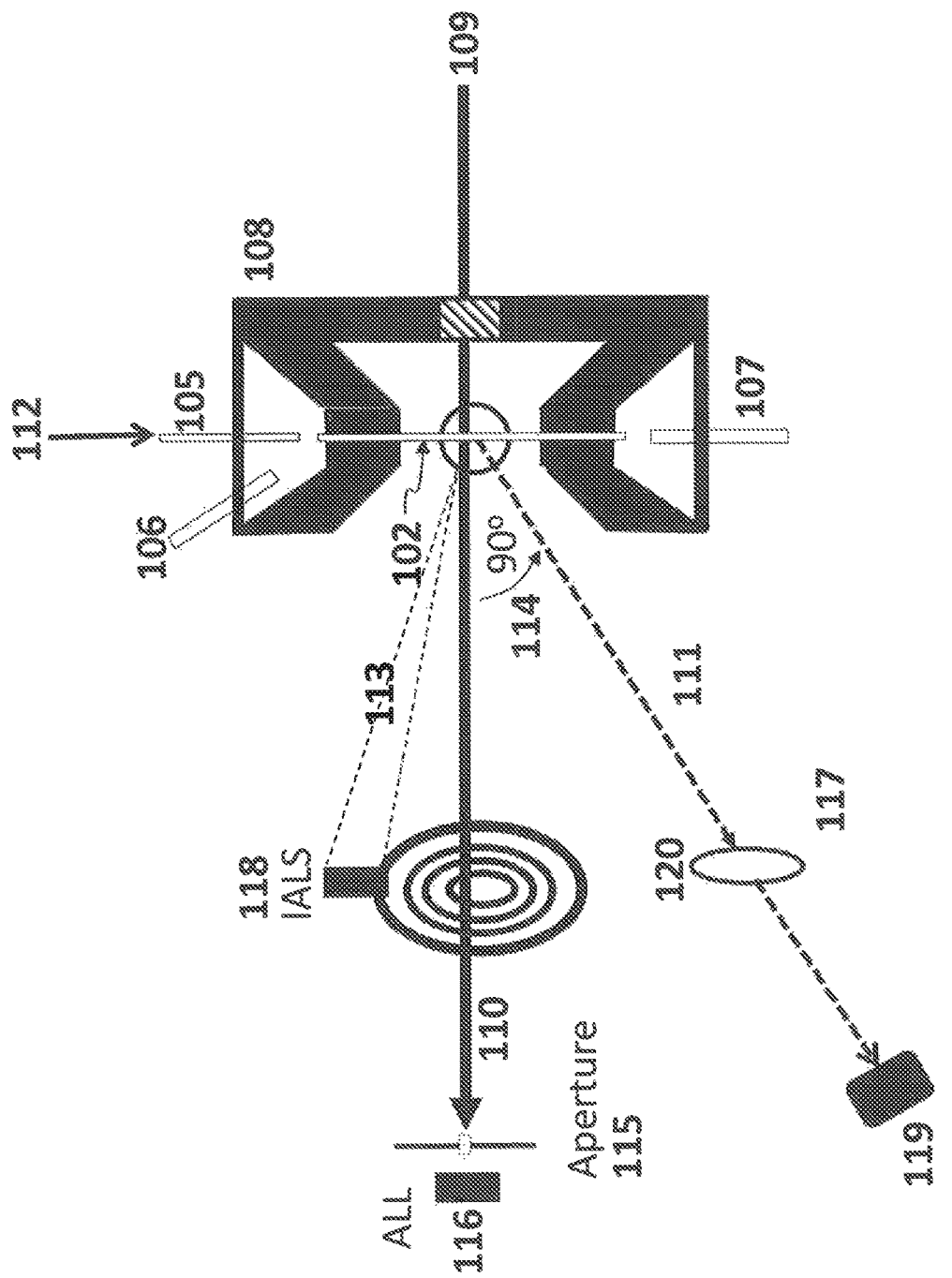

FIG. 4 shows an embodiment of an apparatus having a flow cell having an axial light loss detector, an intermediate angle light scatter detector, and a side-scatter detector, illuminated by an energy source along an axis.

Figure 5:
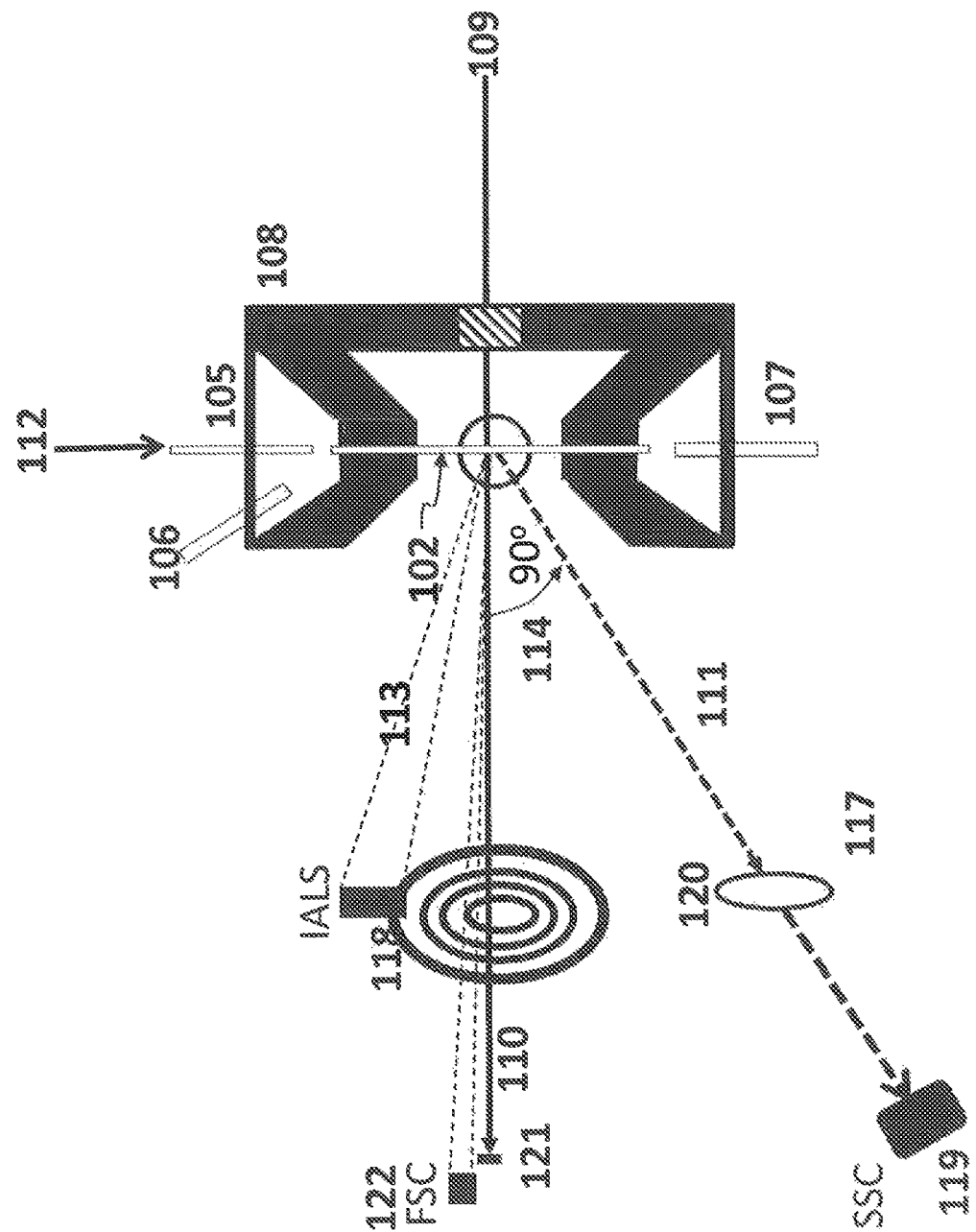

FIG. 5 illustrates an embodiment of an apparatus including a flow cell with a forward scatter detector.

Figure 6:
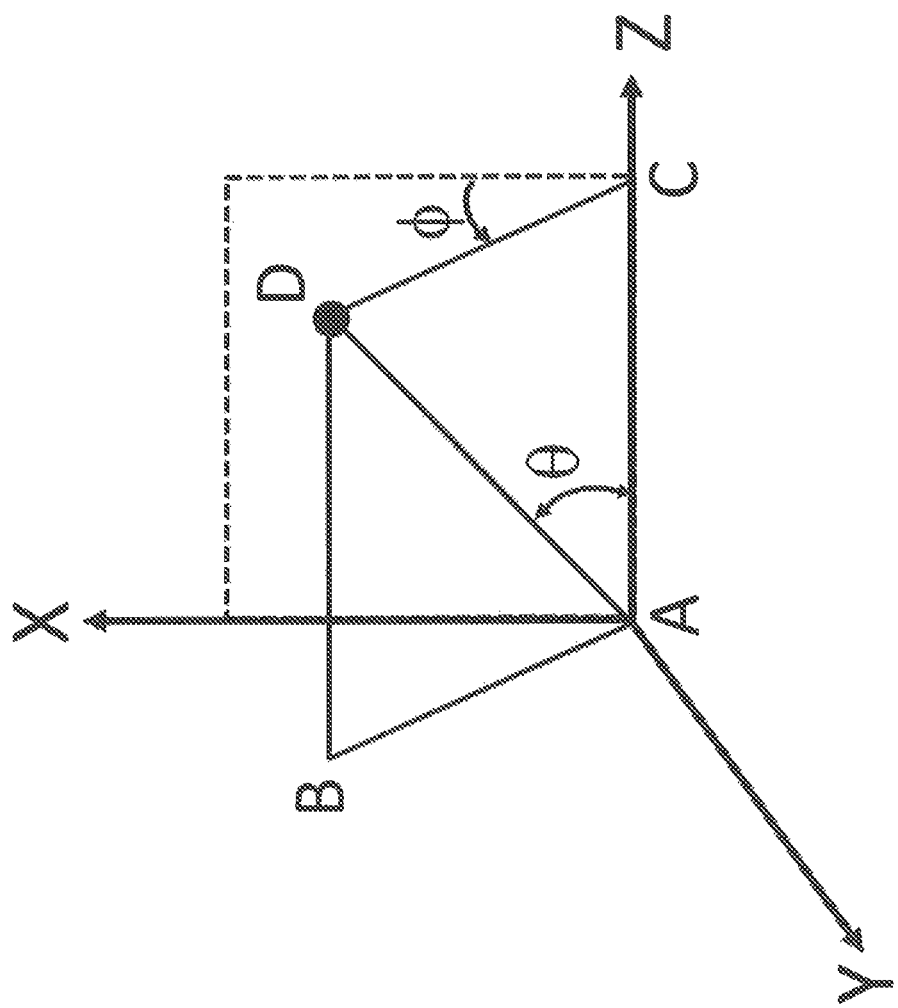

FIG. 6 shows polar and azimuthal angles are measured with reference to an XYZ coordinate system.

Figure 7:
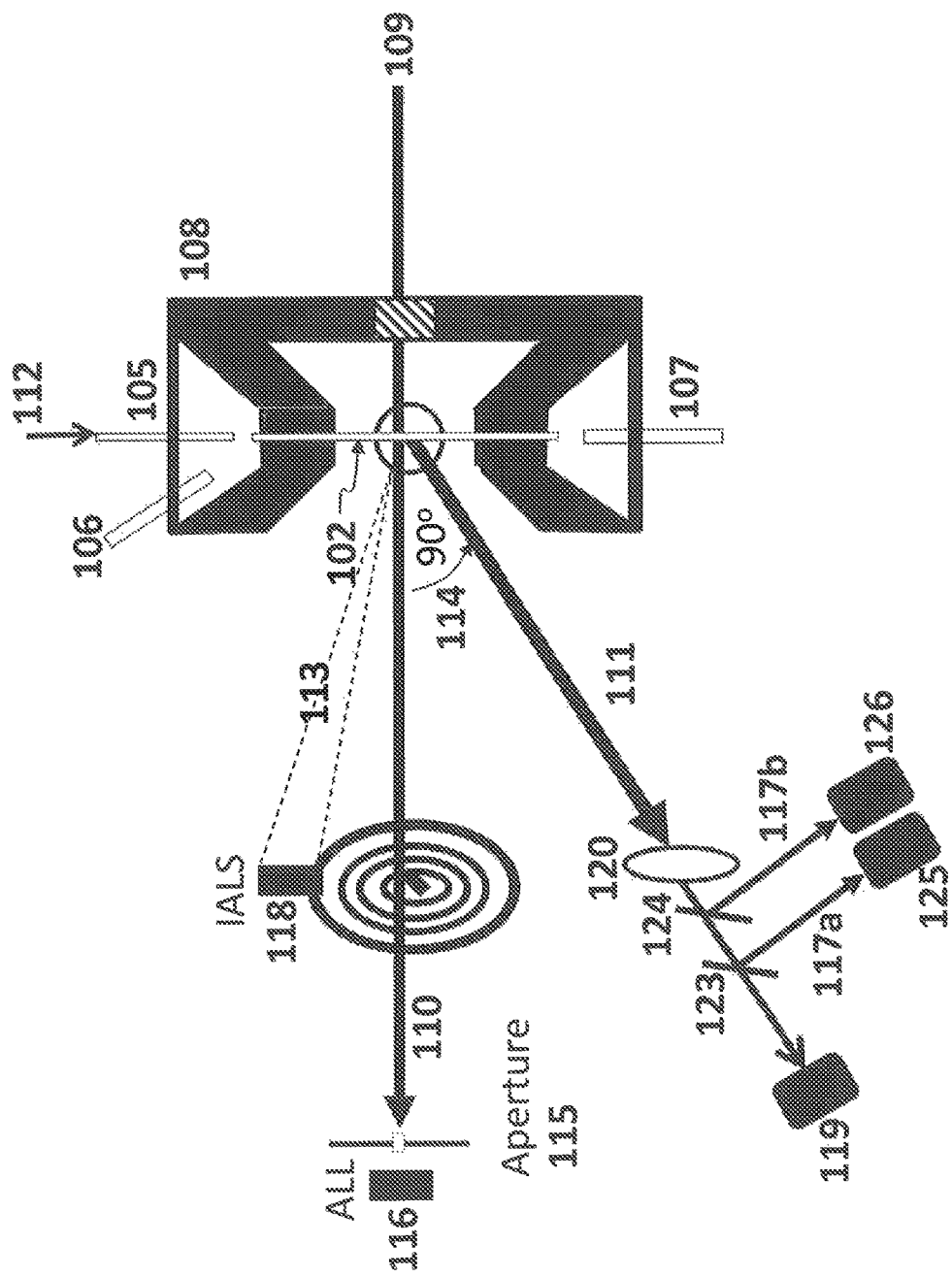

FIG. 7 shows an embodiment of an apparatus with fluorescent detectors.

Figure 8:
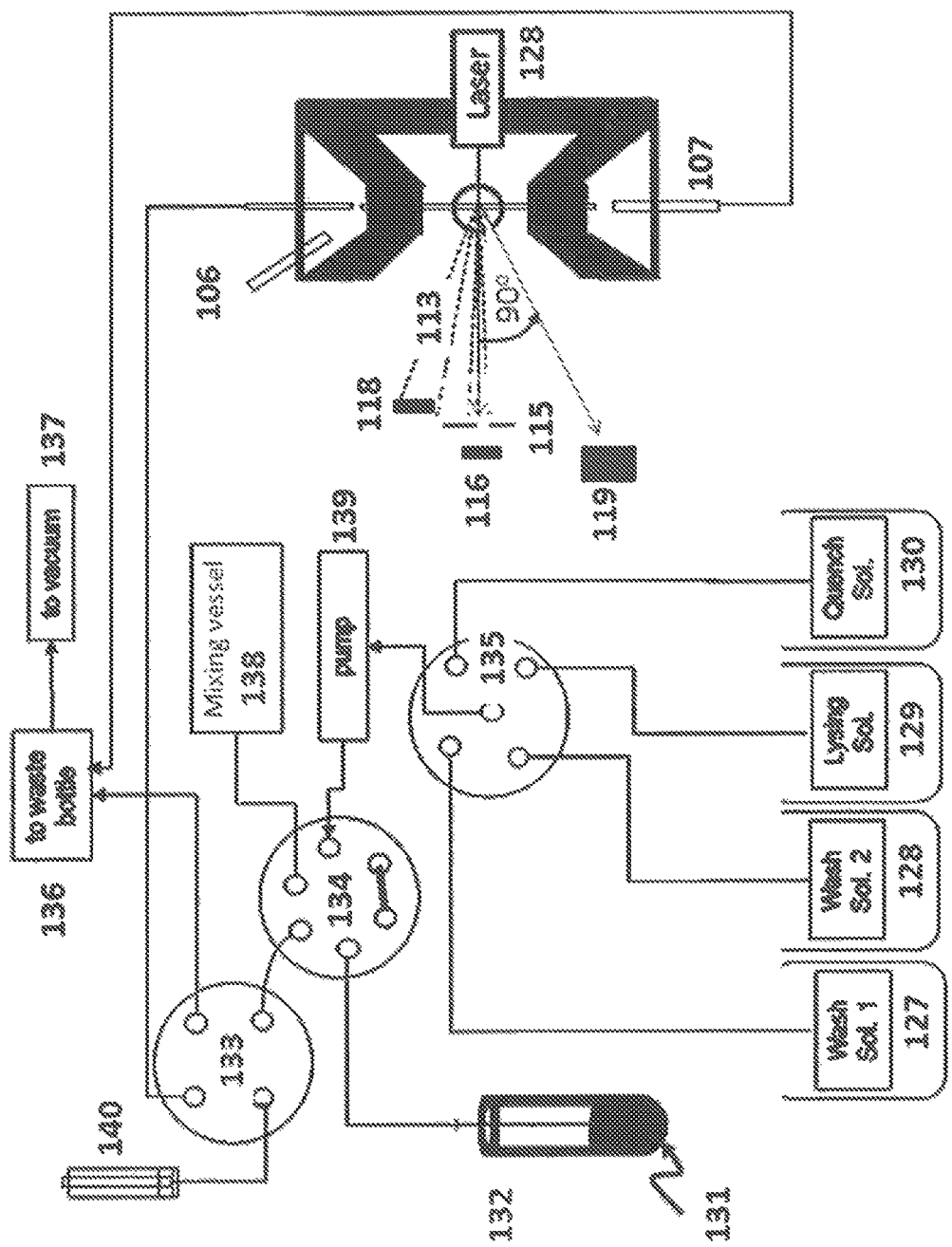

FIG. 8 is a diagram of an embodiment of an apparatus in which the flow cell is integrated to a fluidic system used to perform the hematology workflow.

Figure 9:
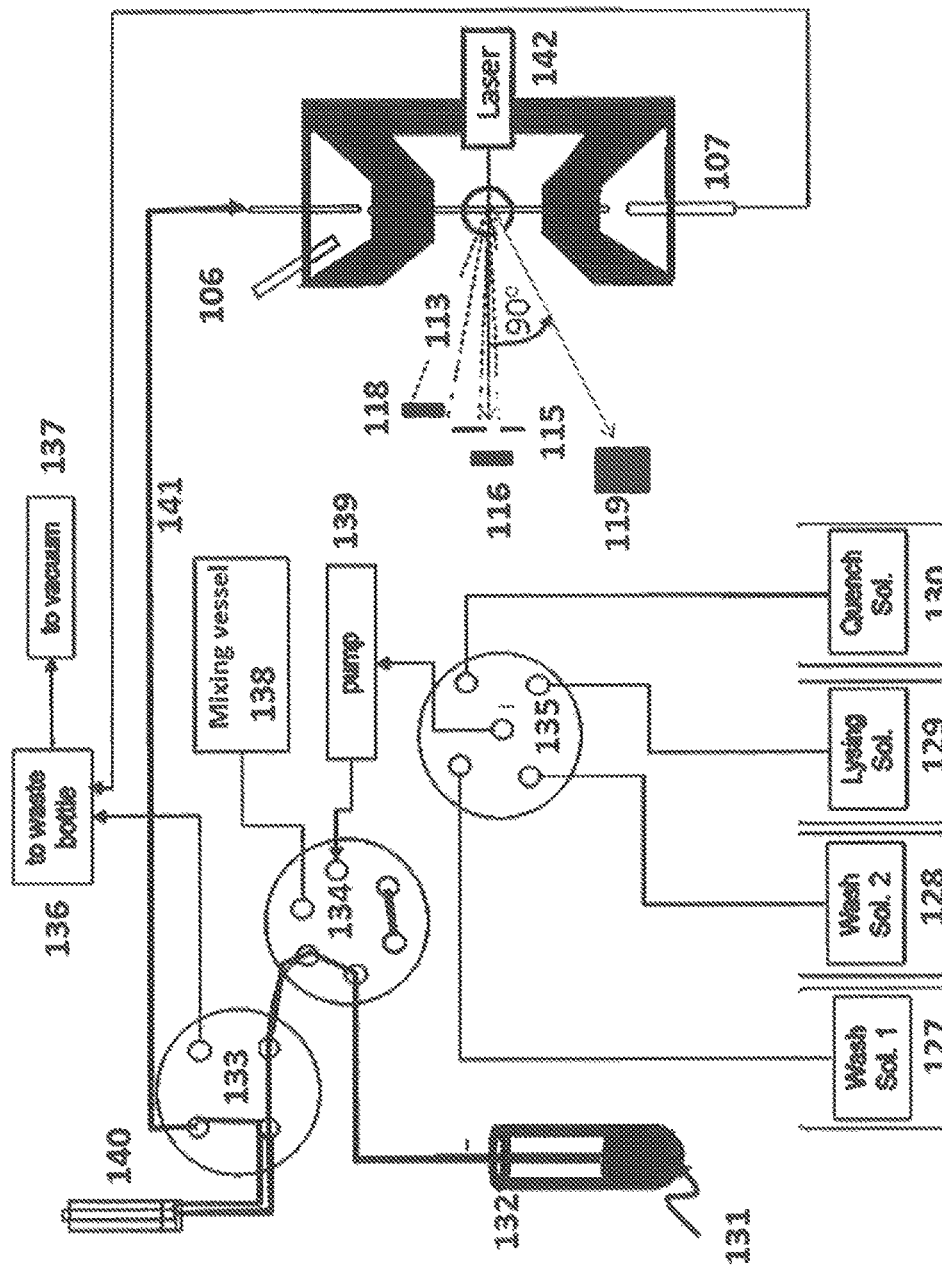

FIG. 9 illustrates an embodiment in which the fluidic system is set to direct the aspirated sample to the flow cell bypassing the sample preparation steps of the hematology operations.

Figure 10:
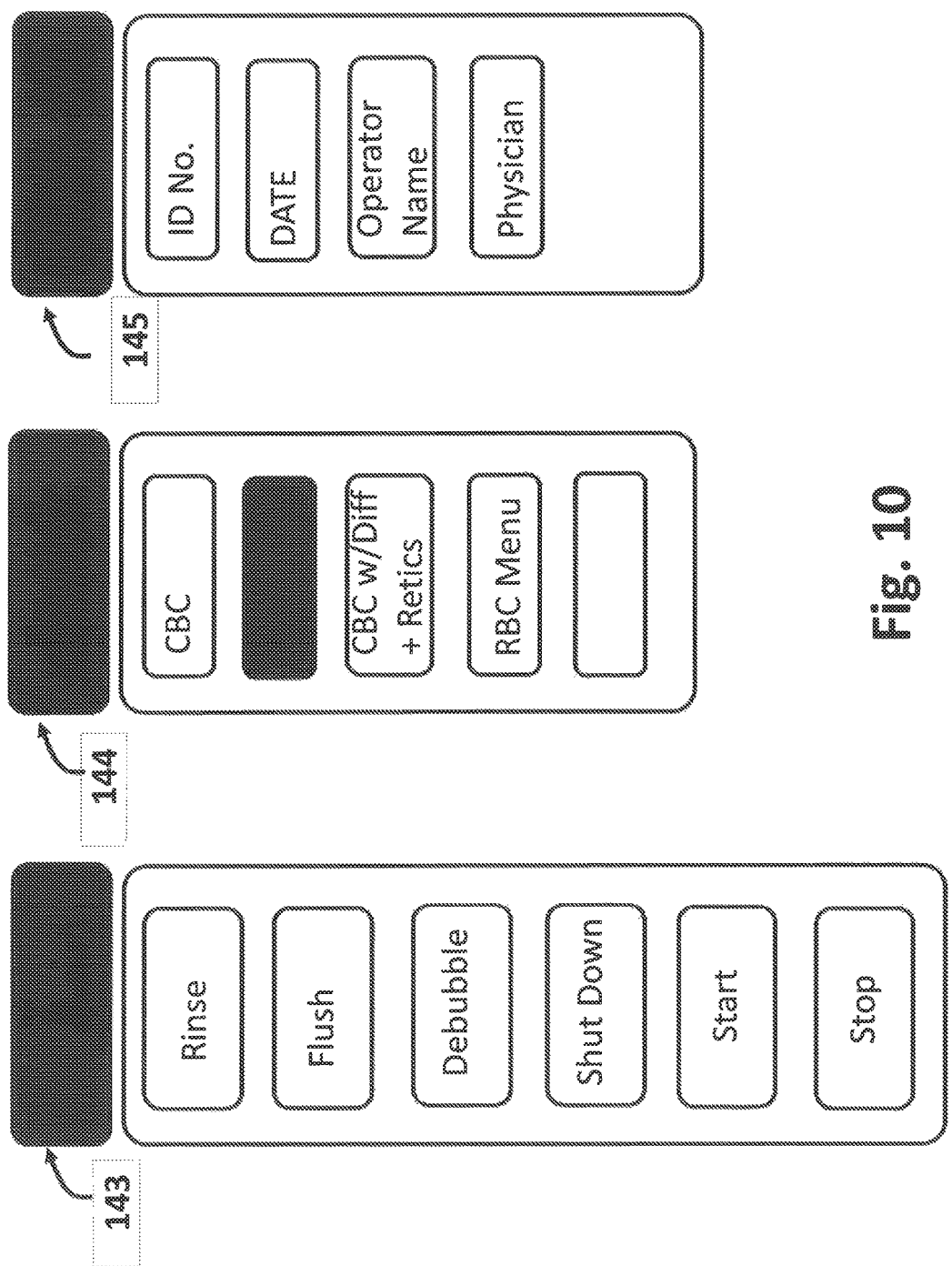

FIG. 10 shows one embodiment of a graphical user interface.

Figure 11B:
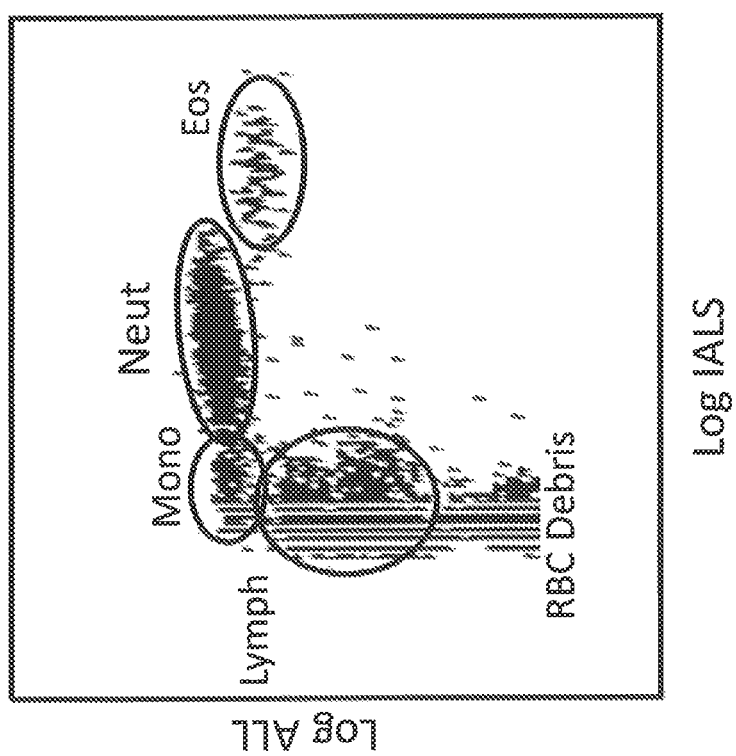
Figure 11C:
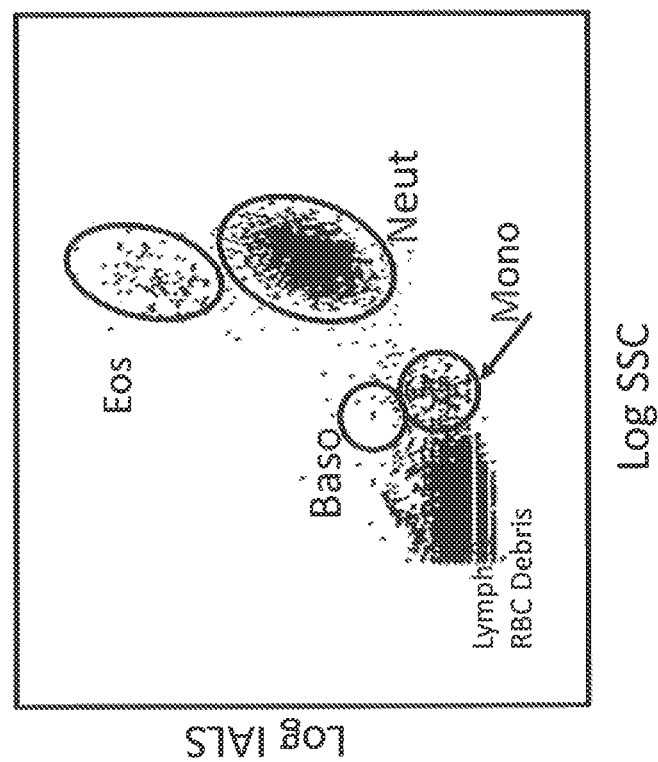
Figures 12A, 12B:
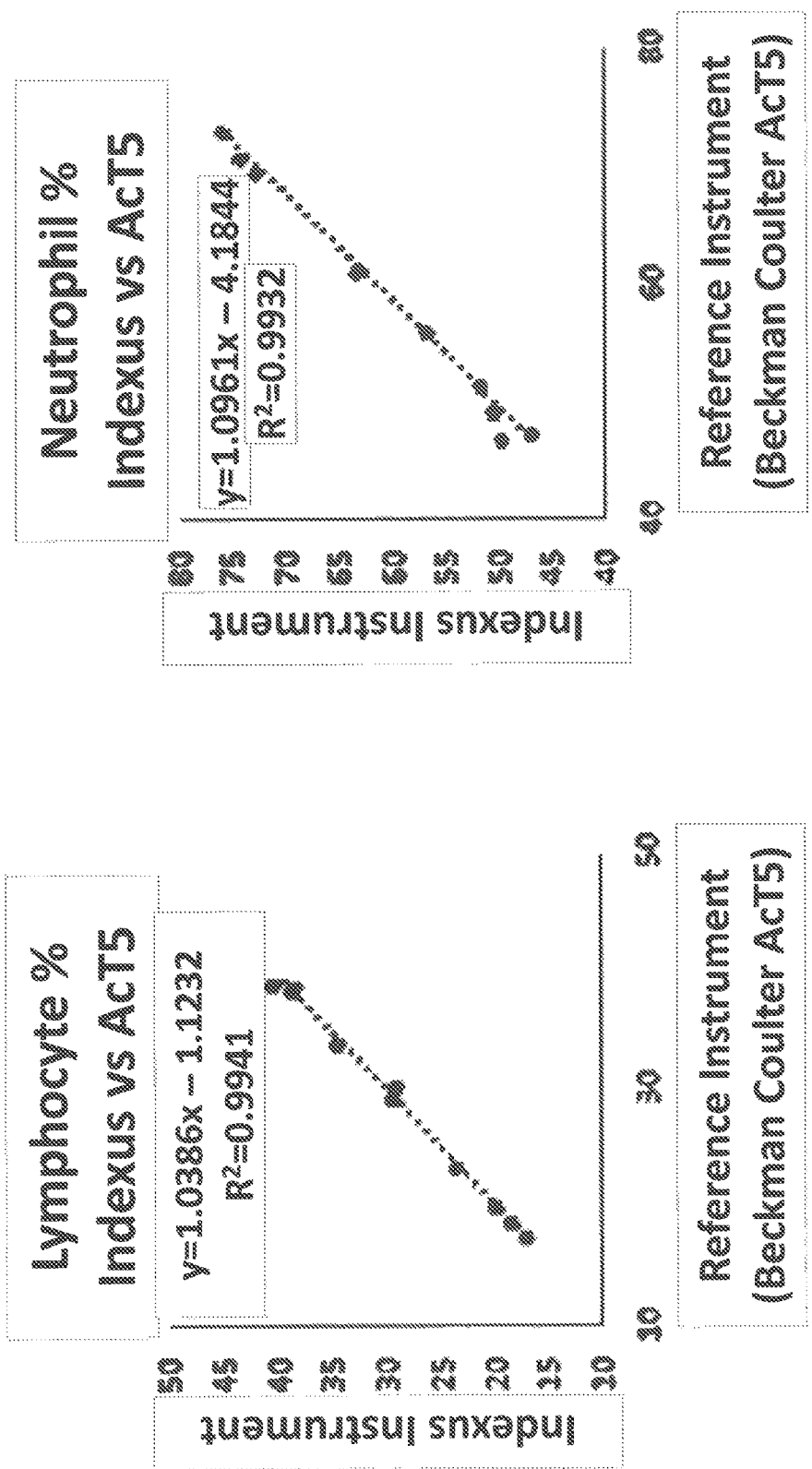
Figure 12D:
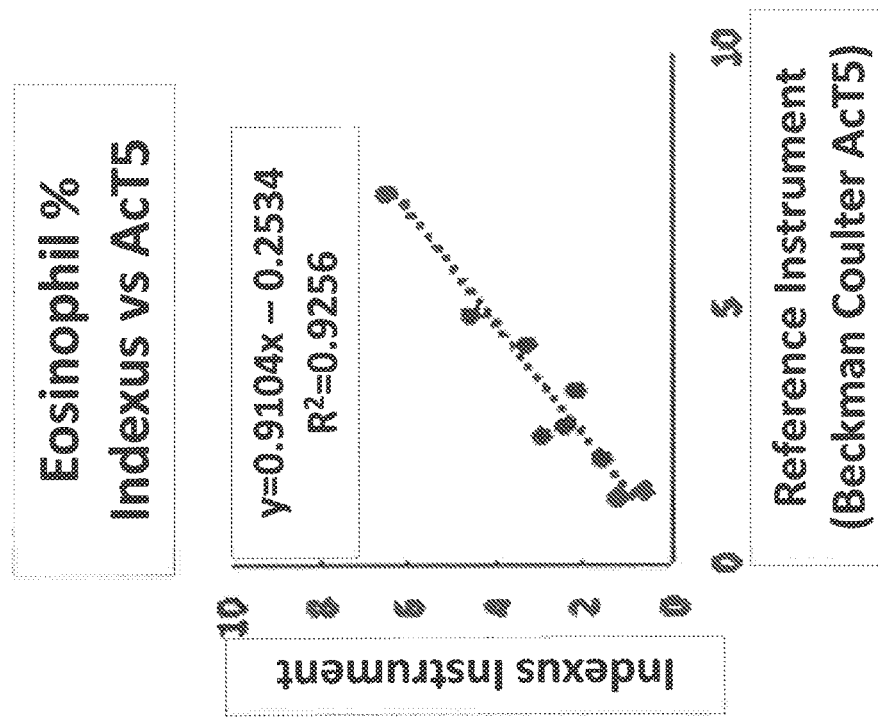
Figure 12C:
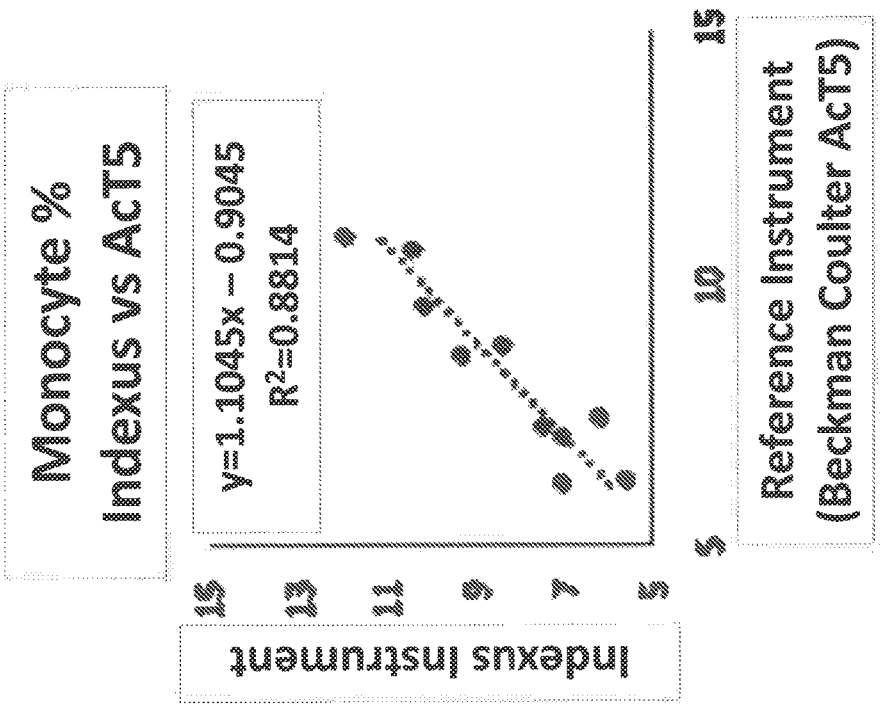
Figure 13A:
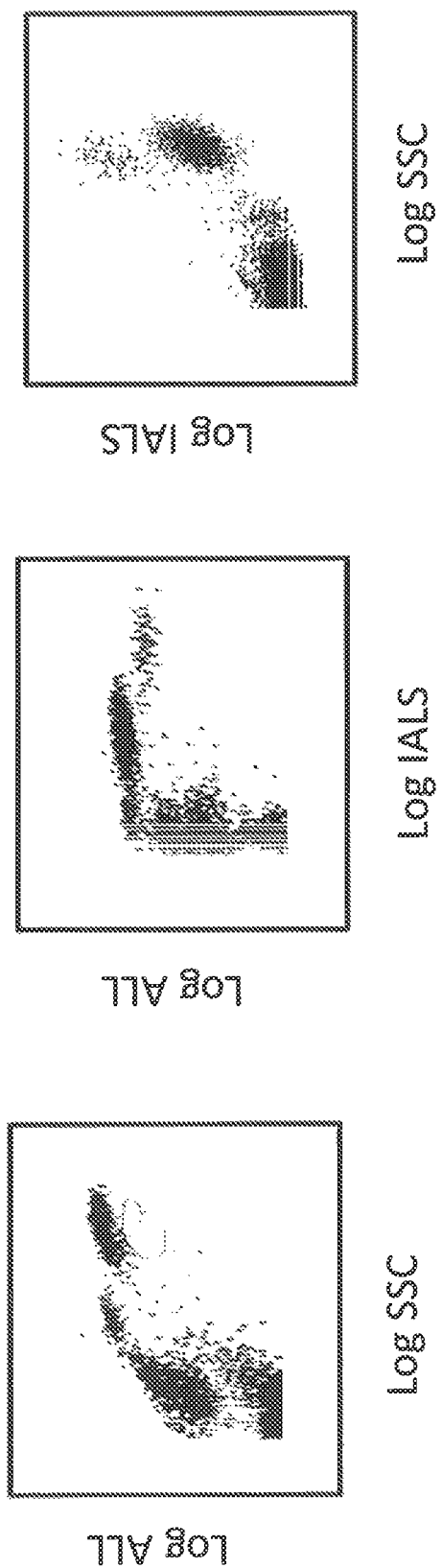

FIGS. 11(A)-11(C) show an example of multiple populations of leukocytes resolved in a whole blood sample exposed to a lytic reagent.

FIGS. 12(A)-12(D) show the correlation between the results obtained by a prototype embodiment of the apparatus and reagents of the present approach, compared to results from a reference instrument.

FIGS. 13(A)-13(E) show analyzed results obtained using a prototype embodiment of the apparatus and reagents of the present approach.

FIG. 14 show analyzed results obtained using prototype embodiment of the apparatus and reagents of the present approach at different pH values.

Figure 15:
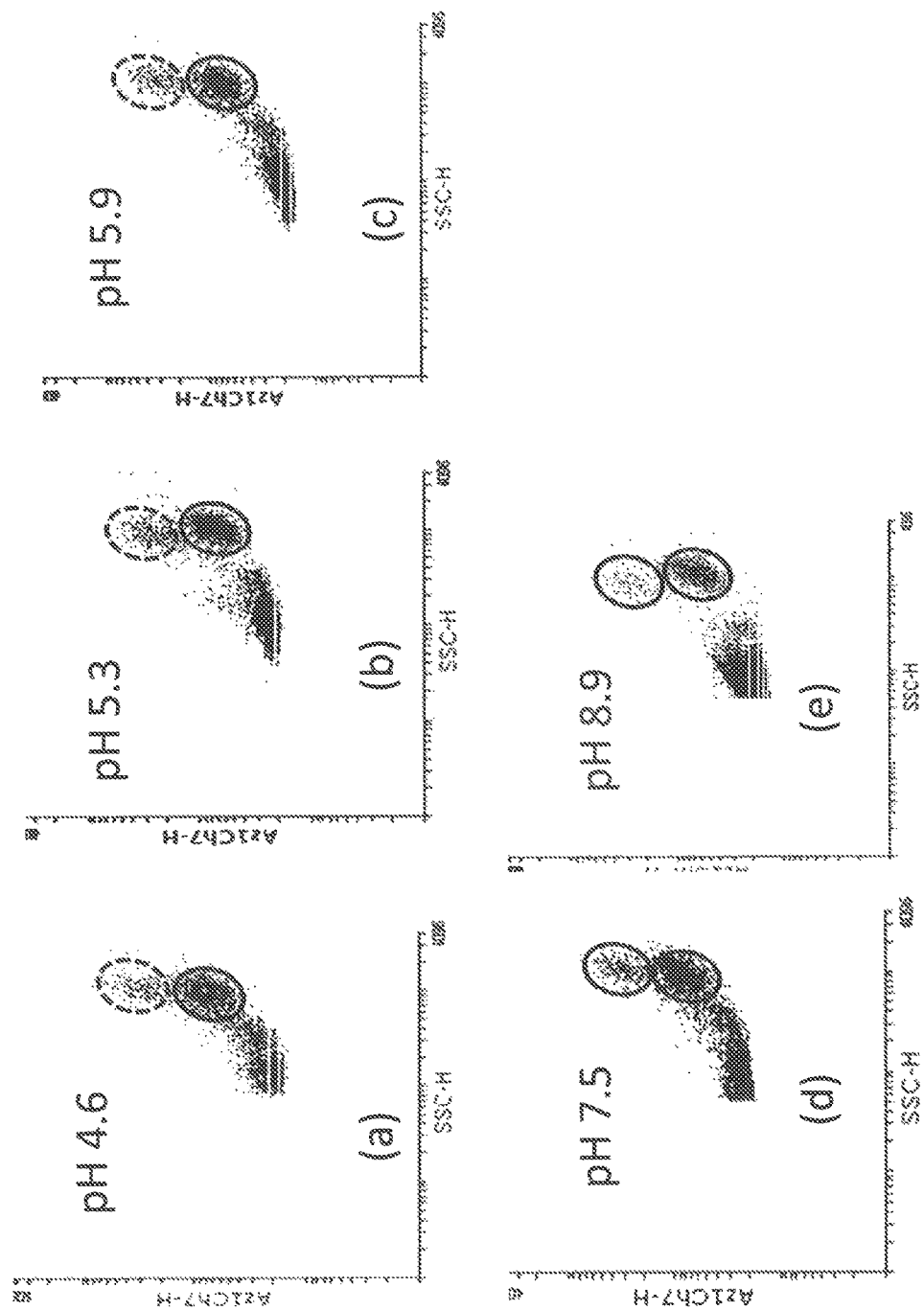
Figure 15F:
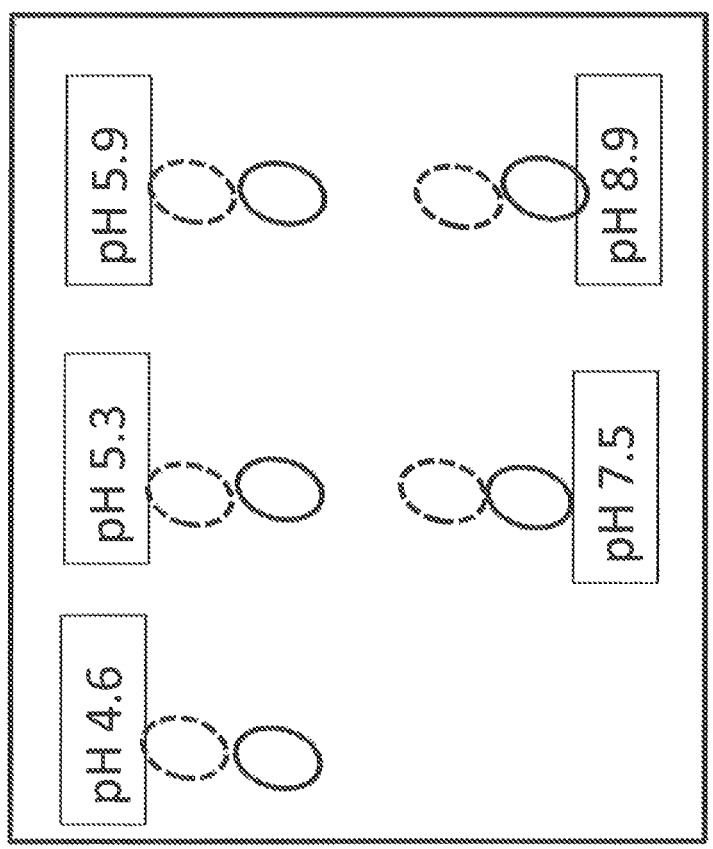

FIGS. 15(A)-(E) show analyzed results obtained using prototype embodiment of the apparatus and reagents of the present approach at different pH values, and FIG. 15(F) shows relative subpopulation positions.

Figures 16A, 16B:
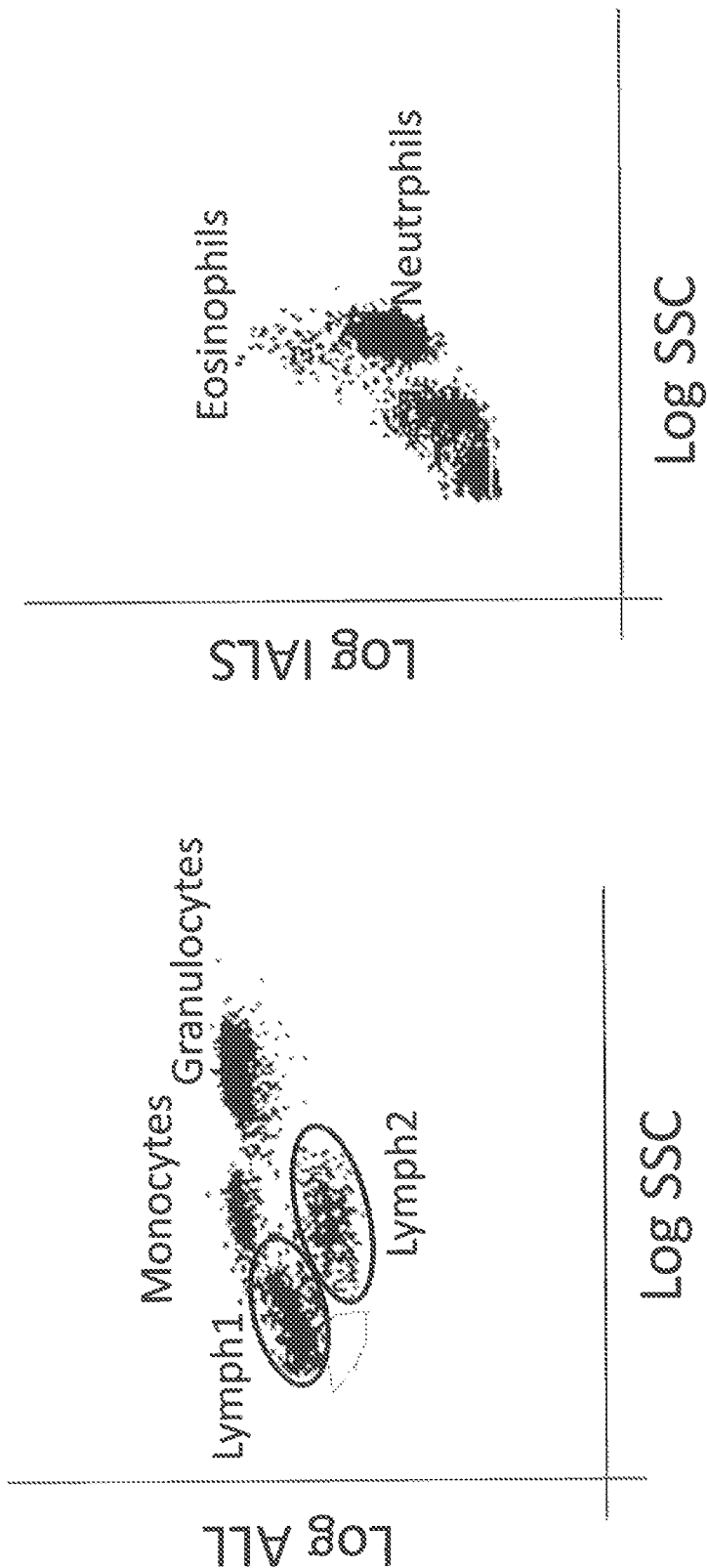

FIGS. 16(A) and 16(B) show analyzed results obtained using prototype embodiment of the apparatus and reagents of the present approach and relative subpopulation positions.

Figures 17A, 17B:
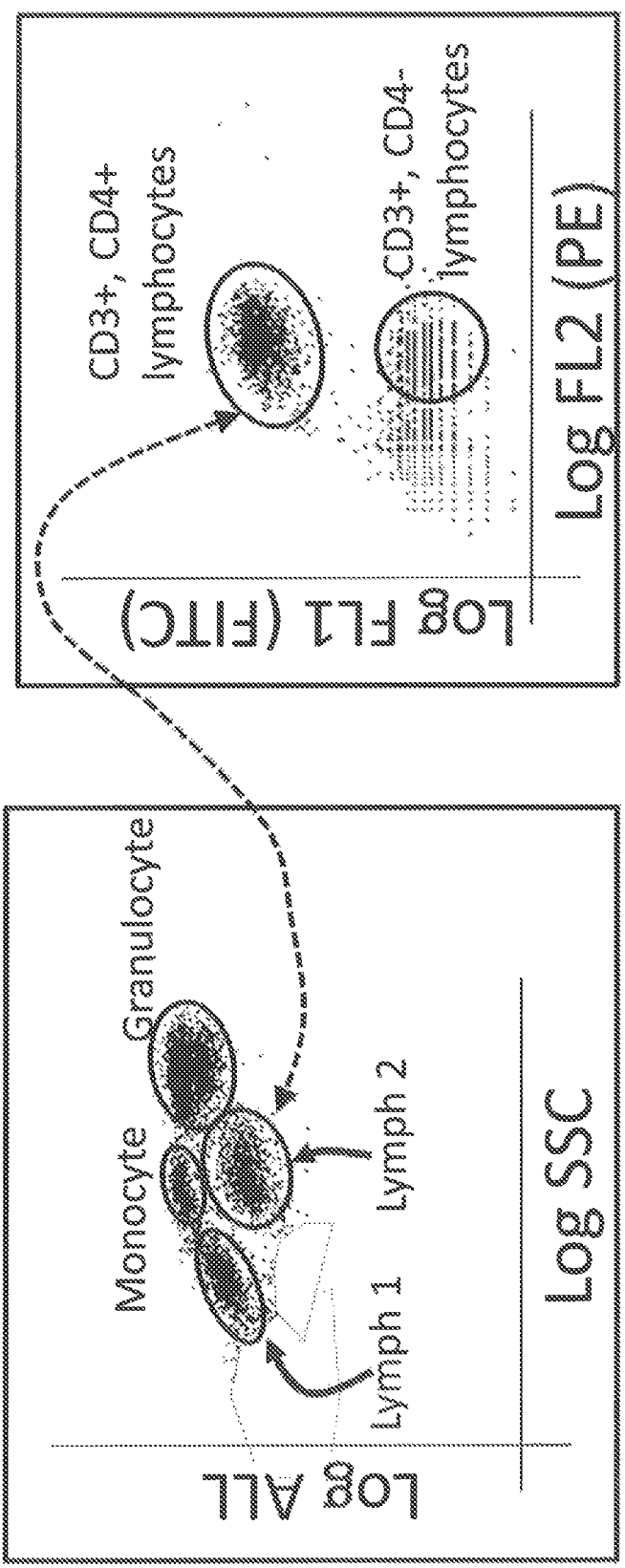

FIGS. 17(A) and 17(B) show analyzed results obtained using prototype embodiment of the apparatus, including fluorescent detectors, and reagents of the present approach and relative subpopulation positions.

Figure 18:
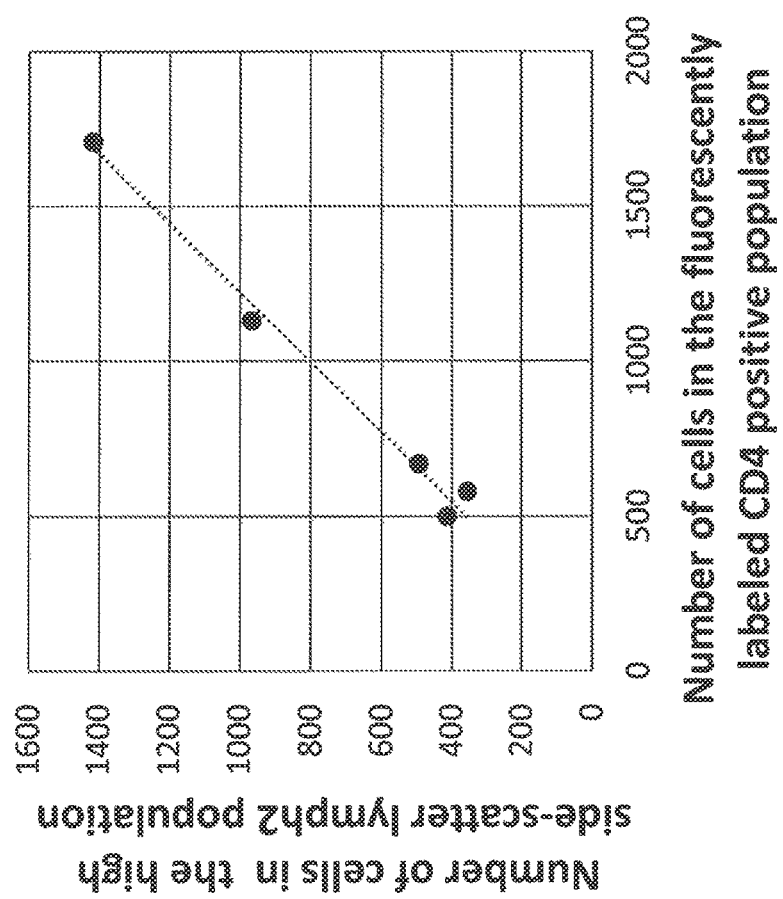

FIG. 18 shows a comparison of the number of cells in CD3 and CD4 positive populations compared with the number of cells in the Lymph2.

Figure 19:
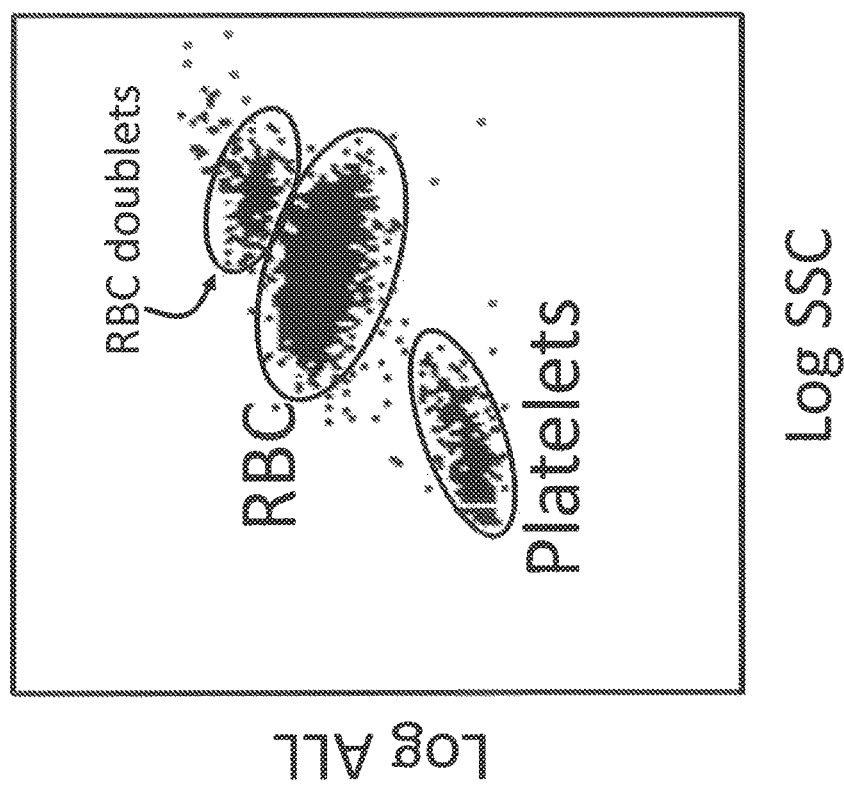

FIG. 19 shows analyzed results obtained using prototype embodiment of the apparatus and reagents of the present approach and relative subpopulation positions.

FIG. 20 shows relative subpopulation positions from analyzed results using prototype embodiment of the apparatus, including fluorescent detectors, and reagents of the present approach.

DESCRIPTION

Disclosed herein are embodiments of optical hematology analyzer apparatus, systems, and methods, for differentiating populations and subpopulations of leukocytes. Some embodiments employ no more than three optical detectors, thereby reducing the cost of embodiments and expanding the potential use of such embodiments at low price points. The present approach allows for a flow cytometry-based platform that utilizes only optical measurements and only three optical detectors configured around an optical flow cell, to identify and enumerate five different populations of leukocytes in a human whole blood sample passing through the optical flow cell and illuminated by a beam of electromagnetic radiation. In some embodiments, two of the optical detectors measure scattered light, and the third detector measures either low angle forward scattered light or axial light loss. For the purpose of descriptions in this document, the detector measuring axial light loss will also be referred to as a light scatter detector. The platelet and red blood cells may be identified and enumerated using light scatter measurements from at least one but no more than two of the three detectors.

In some embodiments, one of the three detectors—the side scatter detector—is positioned to detect light scattered by blood cells or particles in a direction substantially orthogonal to the plane defined by the longitudinal axis of the flow cell, and the axis parallel to the direction of propagation of the electromagnetic radiation (often called "side scatter"). The second detector, the intermediate angle light scatter detector, is positioned to detect light scattered at an intermediate angular range from about 25° to about 45° relative to an axis parallel to the direction of propagation of the electromagnetic radiation. The third detector may be positioned to measure either axial light loss or a low-angle forward light scatter.

In some embodiments, the apparatus may be used as stand-alone instrument analyzing one tube of sample. The sample may be robotically presented or manually presented by a user, to the apparatus, one at a time. In some embodiments, embodiments may be used in a high throughput setting, such as a reference laboratory, by integrating the apparatus with an automated conveyor belt or carrousel providing multiple samples.

In some embodiments, the apparatus may include a flow cell made of one or more optically transparent capillary tubes, and the flow channel may have substantially cylindrical dimensions. In other embodiments the flow cell of the apparatus may be made of one or more optically transparent capillary tubes, and the flow channel may have substantially square or rectangular dimensions. In some embodiments, the apparatus may use a flow cell made from a prism, such as a cuvette tube, and may have, for example, a square or rectangular or triangular cross section.

In some embodiments, some or all reagents necessary to perform one or more assays may be contained on-board the apparatus. In some embodiments, the apparatus may be connected to vessels containing some or all reagents necessary to perform one or more assays.

Figure 1:
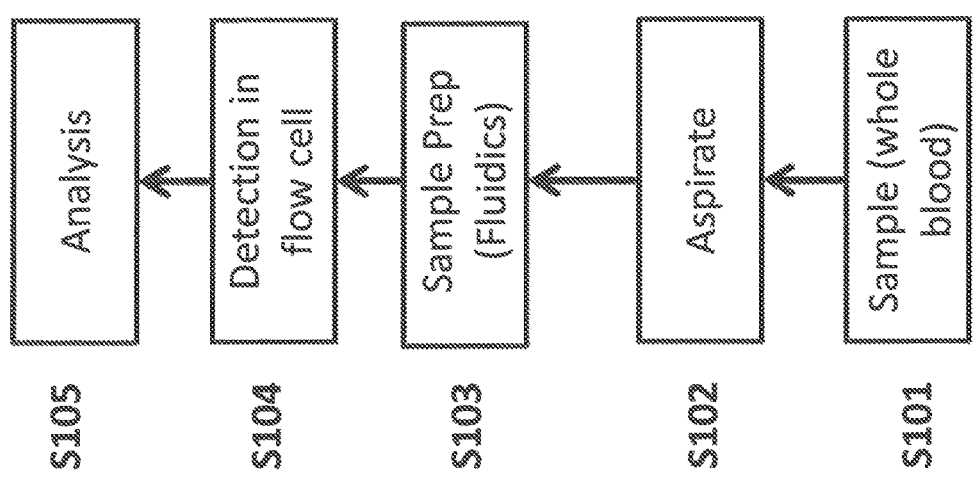
FIG. 1 shows a a block diagram of the workflow for automated hematology analysis.

To illustrate the present approach, FIG. 1 shows the workflow for automated hematology analysis. A controller may be incorporated in an embodiment to control components, such as components in a fluid handling system that may include fluid flow direction devices such as valves and pumps, to achieve the desired workflow. As shown in FIG. 1, in an automated hematology analyzer workflow, whole blood may be presented S101 to the instrument in a sample tube S101, which aspirates S102 a pre-determined volume of the blood using an aspirating tube or needle. Alternatively, a volume of the sample may be aspirated over a predetermined period of time. A controller (e.g., the controller for the fluid handling system, a separate controller, or a combination of controllers) may be programmed to control aspiration. The sample is then processed S103 in an automated sample preparation fluidic module. Afterwards, the processed sample is then detected and measured S104 in a flow cell before being analyzed S105 using a data analyzer employing, for example, signal processing electronics and software.

Figure 2:
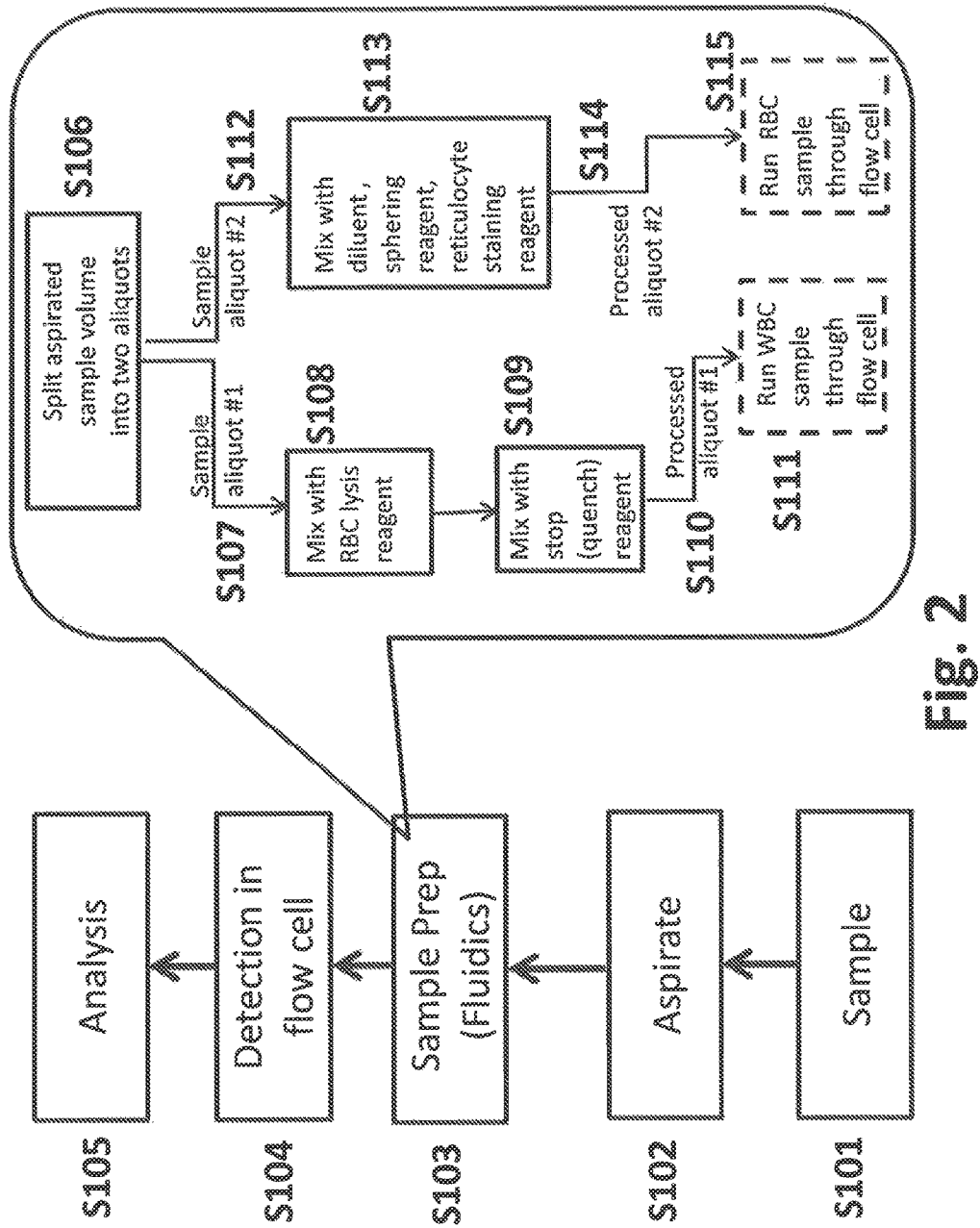
FIG. 2 shows an embodiment of a method for preparing a sample in a hematology analyzer.

FIG. 2 shows an embodiment of a method for preparing a sample in a hematology analyzer. Referring to FIG. 2, the basic sample preparation steps in an automated hematology analyzer may include the splitting of an aspirated blood volume into at least two aliquots S106, a first aliquot or sample aliquot #1, and a second aliquot or sample aliquot #2. Sample aliquot #1 may be directed S107 to a mixing cup where it is mixed with a lytic reagent S108, followed by another solution to stop the lytic reaction, such as a quenching solution S109. In some embodiments, the step S109 may be skipped. The resultant mixture in aliquot #1, now containing intact white blood cells and lysed red cell debris, may then be directed to a flow cell S110, where the contents are hydrodynamically focused to run through the flow cell in seriatim S111. In some embodiments, the contents may be acoustically focused instead of hydrodynamic focus. The contents may subsequently be detected by, for example, optical means S104, and analyzed S105 using an analyzer employing, for example, signal processing electronics and software. In some embodiments, the sample may be exposed to a quenching solution after the lytic reaction but prior to the measurement in the flow cell. Sample aliquot #2 may be directed to a mixing cup S112 where it is mixed with reagents S113 that comprises a diluent which may or may not additionally include components that substantially render the red blood cell (RBC) spherical in shape and also a RNA staining fluorescent dye that penetrates the membrane of the RBC to bind to the RNA of the immature RBCs commonly known as the Reticulocytes. In some embodiments, the diluent may be a non-lysing diluent. The diluent does not lyse red blood cells and may have a non-ionic detergent in a substantially isotonic solution. Generally, for the purpose of the descriptions in this disclosure, an isotonic solution refers to solutions having a similar osmotic pressure across a semipermeable membrane of blood cells. The resultant sample mixture may then be directed to a flow cell S114, where the contents are hydrodynamically focused to run through the flow cell in seriatim S115. The contents may subsequently be detected by, for example, optical means S104, and analyzed S105 using an analyzer employing, for example, signal processing electronics and software. Apparatus embodying the present approach may be pre-programmed to operate pursuant to this method for a specific assay, and operate as a closed system or a closed workflow. Embodiments may include a controller for controlling operation of the apparatus, such as the operation of a fluid handling system, to achieve the desired workflow. The closed system for automated hematology analysis may be useful for ensuring repeatability and precision of results and to avoid human error Embodiments of the present approach may feature a single optical transducer that includes the flow cell and optical detectors for light scatter, and an illumination source. The illumination source may also be separate but connectable to the optical transducer. Referring to the embodiment shown in FIG. 3(a), flow cell 108 features a flow channel 102, a flow cell body 103, a sheath fluid insertion tube 106, a waste removal tube 107, and a sample insertion tube 105. The sheath fluid hydrodynamically focuses the fluid stream that flows through the flow channel 102. The insertion tubes 105 and 106 may be fluidly connected to a first end of the flow cell body 103, such that sheath fluid and sample may flow into the flow channel 102, e.g., via pump (not shown). The flow cell body 103 may optionally feature a first void space, such that sheath fluid and sample to flow into the void space at desired flow rates, mix, and then flow into the flow channel 102. The waste removal tube 107 may be fluidly connected to a second end of the flow cell body 103, such that sheath fluid and sample that have flowed through the flow channel 102 may exit the flow cell 108. The flow cell body 103 has an opening or a through hole 104 to allow a beam of light (alternatively referred to as electromagnetic radiation) from an illumination source to pass through it and intersect the capillary 102. The through hole 104 may be a physical gap in flow cell body 103, or alternatively may be a material that allows light from a source of electromagnetic radiation alternatively referred to as a light source (not shown) to pass through and illuminate the flow channel 102

(in the embodiment shown, flow channel 102 is a capillary tube). In some embodiments, the light source may be one or more lasers, one or more lamps, or one or more light emitting diodes, or any combination thereof. In some preferred embodiments, the laser may be a solid-state laser, a gas laser or a diode laser. In some other embodiments, in the solid state laser the lasing medium may be pumped by a diode laser, generally known as a diode pumped solid state laser or DPSS.

In some embodiments, the flow channel may be a capillary tube. The capillary tube may be substantially cylindrical, such as a cylinder with an inner diameter equal to or greater than about 75 micron, but less than or equal to about 250 micron, and may have a length greater than about 1 mm. In some embodiments the length of the flow channel may be less than 1 mm. In some embodiments, the flow channel may also be a prism. For example, in some embodiments the flow channel may be a flow-through cuvette, such as a cuvette having a square cross section 102b, as shown in FIG. 3(b). Such a cuvette is also represented separately, 102c, on the left side of FIG. 3(b). In some embodiments, the flow channel may be fabricated on a solid substrate. The signals in some embodiments may be excited by an illumination source emitting electromagnetic radiation, for example radiation in the red wavelength range of the visible spectrum, and as another example, in the blue-green wavelength range of about 405-540 nm. In some embodiments the illumination source is a diode laser. In another embodiment, the illumination source may be a laser, such as a laser emitting in the wavelength range of about 630 nm-650 nm, for example. In other embodiments, two or more lasers may be used. In some embodiments, one or more parts of the laser 142 may be physically connected to the flow cell as shown in FIG. 8 and FIG. 9

FIG. 4 shows an embodiment of a flow cell 108, an axial light loss (ALL) detector 116, intermediate angle light scatter (IALS) detector 118, side-scatter (SSC) detector 119, the flow cell 108 illuminated by laser beam 109. When a cell or particle flowing through the flow channel 102 passes through the laser beam 109, the light is scattered in various directions. The axial light loss detector 116 is placed directly behind an aperture 115, with both 116 and 115 aligned along the axis 110 of the laser beam 109. The side scatter detector 119 is positioned to collect light scattered by illuminated particles, such as blood cells or any other particle flowing through the flow cell, in a generally orthogonal direction 114 to both the laser beam axis 110 and the direction 112 of the flow of the particle in the flow channel 102 of the flow cell 108. The range of angles over which the SSC detector 119 measures scattered light may be from about 75° to about 105°, generally within a light scatter cone of about 30°. In embodiments this range may be greater than 30°. In some embodiments this can be about 50°. An intermediate angle light scatter detector 118 may be positioned to detect light scattered 113 by an illuminated cell or a particle, flowing through the flow channel 102 of the flow cell 108, at angles from about 25° to about 45° measured relative to the laser beam axis 110.

The angular distribution of the scattered light depends on the size, shape, internal structure and refractive indices of the said cells or particles. Generally, low angle light scatter provides information that is representative of size, while high angle light scatter, for example 90° light scatter, offers information on structural complexity of the particles. However, such generalization is limited because theoretical calculations have shown that intensity of scattered light for a given particle is represented by an undulating function of the scatter angle. For particles with complex structures, such as white blood cells, the angular distribution is even more complex. As a result, in order to maximize the ability to distinguish between different cell types of substantially similar size, for example various subpopulations of white blood cells, careful empirical experimentation is required to define the locations of light scatter detectors that provide the necessary differentiation between targeted cell types. It is worth noting here that various environmental conditions influence the size and shape of the cells also. Therefore, in order to obtain the optimum differentiation between different cell types, the detector locations must be determined in conjunction with reagent conditions to which the said cell may be subjected during or prior to a measurement. In one embodiment, scattered light may be detected in three angular ranges ALL, SSC, and IALS to differentiate five different leukocyte populations, namely lymphocytes, neutrophils, monocytes, eosinophils and basophils. In embodiments, ALL and SSC detectors may be used to identify red blood cells and platelets, and also at least three leukocyte populations. In another embodiment, ALL and IALS detectors may be used to identify four different leukocyte populations, lymphocytes, neutrophils, eosinophils and monocytes. In one embodiment, IALS and SSC detectors may be used to differentiate between neutrophils and eosinophils. In embodiments, the ALL detector may be replaced by a forward scatter detector (FSC) 122 that detects scattered light within the angular range from about 0.5° to about 3° (FIG. 5). An obscuration object 121 is placed directly in the path of the transmitted laser beam. In embodiments the FSC detector measures scattered light from about 1° to about 3°. In some embodiments the FSC detector measures scattered light from about 1° to about 2°.

FIG. 6 generally describes, using a geometric schematic, the definition of polar and azimuthal angles. In one embodiment, the detector used to detect light scattered at an intermediate angular range as described herein, is positioned to measure scattered light traveling at a polar angle of about 43° and azimuthal angle between 0°-90°, and preferably 20°-50°, and most preferably between 30°-35° where the polar and azimuthal angles are measured with reference to an XYZ coordinate system as shown in FIG. 6, where the origin is at the point of illumination of the flowing blood cell, Z axis is along the direction of the laser beam and the X axis is along the axis of the flow cell which is the same as the direction of flow of the blood cell through the flow channel. As one skilled in the art would recognize, the azimuthal angular ranges of 90°-180°, 180°-270°, or 270°-360° would work in a similar fashion as the range 0°-90°. The preferable azimuthal angular range 20°-50° could be replaced by the angular ranges 130°-160°, or 200°-230°, or 310°-340°.

In some embodiments, as shown in FIG. 7, in addition to the light scatter detectors, the apparatus further includes fluorescence detectors 125, 126 to measure fluorescence emitted from a blood sample flowing through the flow channel. For example, fluorescence detectors 125, 126 may detect fluorescence light in a direction substantially orthogonal to both the direction 110 of the laser beam 109 and the direction of flow 112 of the cells or particles in the flow cell. The fluorescent light in this direction 111 may be transmitted through optical lens system 120 and resolved into multiple spectral ranges 117a, 117b using optical filters 123, 124. One of ordinary skill would appreciate that an apparatus according to the present method may feature a different number of spectral ranges, optical filters, angular ranges and detectors.

FIG. 8 shows an embodiment according to the present approach in which the flow cell 108 is further integrated to a fluidic system used to perform the hematology workflow. The fluidic system depicted in FIG. 8 is demonstrative of a fluid handling system that may be incorporated into an embodiment of the present approach, and may be used to control fluid flow through the embodiment (e.g., volume, direction, rate, etc.), such as to achieve a desired workflow (e.g., open or closed, depending on the desired protocol). In the embodiment shown, the system includes valves 133, 134 and 135, pump 139, syringe pump 140, mixing vessel 138, and vacuum source 137. These components may be fluidly connected, such that fluid (e.g., a sample) may flow from one component to another without exposure to external conditions, without contamination, sourced from outside the components, and/or without leakage or spillage of fluid. Two components in fluid connection may have intermediate components also in fluid connection, such as, for example, two valves in fluid connection may have a pump between the valves that is in fluid connection with each valve. A fluid handling system may incorporate such components, and a controller may be used to control operation of the fluid handling system or a subset of components, to achieve a desired workflow. Reagents may be included with the system, and may be contained in, for example, different reservoirs 127, 128, 129 and 130. Waste bottle 136 is connected to a vacuum pump 137 and the waste tube 107 of the flow cell. In some embodiments, the vacuum pump 137 may be replaced by other types of pumps. The sheath fluid tube 106 is connected to reservoirs containing sheath fluid and a pump (not shown in this figure). Sample 131 is contained in a sample tube 132. In this embodiment, the fluidic handling system includes valves 133, 134, 135 that may be multi-port valves each of which can be set electronically by a controller to route different fluids in more than one or two different directions or flow paths during a single workflow (using pumps or gravity, and/or other devices to force fluid flow in the desired direction, at the desired rate). In some embodiments, the fluidic system may include valves that route a fluid in only or two directions. In some embodiments, the fluidic system may include valves that are combination of the two or more different types of valves. In yet other embodiments, the fluidic system may comprise fluidic circuits embedded in plastic manifolds. In some embodiments, the fluidic system may comprise microfluidic circuits. In some other embodiments, the microfluidic circuits may utilize droplet based electro-wetting methods to control some portions of the flow of fluids. Although not shown in FIG. 8, fluorescence detectors may also be included in the system, in addition to light scatter detectors. Also, although not shown in FIG. 8, in embodiments the cells or particles in the sample stream may be focused to flow in a narrowly constrained path in the flow channel using a piezo electric transducer instead of sheath fluid. As one skilled in the art will appreciate, the above description is only to provide an example of a fluidic handling system to execute a protocol. Other configurations may be utilized to provide for more simple or more complex fluidic operations, such as for example, to run only one or more than one assay protocols. In embodiments, the system may have more than one mixing vessel.

FIG. 9 shows an embodiment in which the fluidic system is set to direct the aspirated sample to the flow cell bypassing the sample preparation steps of the hematology operations described in FIG. 8. In the configuration shown in FIG. 9, fluid flow bypasses the valve 135 and the hematology reagent reservoirs 127, 128, 129, 130, as shown by the dark arrow 141. This embodiment allows the system to analyze samples that are prepared externally.

Laser 128 in FIG. 8 and laser 142 in FIG. 9 are shown as physically connected to the flow cell body. It should be appreciated that in some embodiments the laser may be separate from the flow cell body, and otherwise disconnected from structure supporting the flow cell.

In embodiments, an apparatus according to the present approach can be used to select a work flow from a Graphical User Interface (GUI). FIG. 10 shows an exemplary embodiment of a GUI, comprising a user activated GUI panels for Systems Operations 143, Methods Selection 144 and Patient (Sample) Information 145. Using the tabs under the Methods Selection 144, specific protocols may be activated, such as for example only, the protocol for Complete Blood Count (CBC) or CBC with five-part leukocyte differential. Similarly, specific systems operations 143 such as rinsing the system fluidics (Rinse) or removal of bubbles in the fluidic lines (Debubble), or shutting down the system (Shut Down) can be activated by selecting each operation manually using the GUI. The GUI may include options for a user to program a custom assay or a custom set of systems operation protocols, such as a custom protocol user interface. A custom protocol user interface may be a GUI that permits a user to define a protocol, such as a hematologic protocol or a flow cytometer protocol. The defined protocol may include a number of defined variables, such as, for example, defined flow direction(s), flow rates, sample volumes, reagent volumes, mixing times, etc., such that the user may instruct one or more controllers operating the fluid handling system with the steps necessary to prepare one or more samples pursuant to the protocol, and also (if desired) direct the sample(s) to a flow chamber for analysis. The custom protocol may include instructions to automate the protocol for multiple samples. Alternatively, the software of the system may be configured such that multiple samples can be run sequentially without user intervention.

FIGS. 11-21 shows demonstrative examples of various uses of reagents and methods described herein, in identifying different leukocyte populations, red blood cells and platelets using not more than three of the detectors selected from the group comprising SSC, IALS, ALL and FSC at any given time. These drawings use shorthand notations to identify various populations (e.g., "lymph" for lymphocyte, "mono" for monocyte, "gran" for "granulocyte", "baso" for basophil, and "eos" for eosinophil).

EXAMPLE 1A

FIG. 11 shows an example of multiple populations of leukocytes resolved in a whole blood sample exposed to a lytic reagent comprising a 30 mM solution of NaCl, 0.001% (w/v) of surfactant sodium dodecyl sulfate (SDS), 4.6 mM $K_2HPO_4$, 0.74 mM $KH_2PO_4$, and 0.1% BSA in an aqueous solution at pH 7.5. It should be appreciated that in some embodiments the lytic reagent may comprise a surfactant and an alkali metal salt in a hypotonic solution of different osmolality. A hypotonic solution is any solution that has a lower osmotic pressure than another solution (in this case, blood). In this example, 12.5 microliter (μl) of whole blood collected in EDTA was mixed with 250 μl of the above reagent, incubated for about 30 seconds and run on the apparatus of the present approach. ALL, SSC and IALS were measured for the above sample and plotted pair-wise as shown in FIG. 11. Eosinophils were clearly differentiated from neutrophils by comparing ALL-vs-IALS signals in plot (b), and IALS-vs-SSC signals in plot (c). Lymphocytes, monocytes, basophils and granulocytes can be identified by comparing ALL versus SCC. Lymphocytes, monocytes, neutrophil and eosinophil can be identified by comparing ALL versus IALS. We note that as expected, ALL-vs-SSC generally does not resolve the eosinophil population from the neutrophil population in human blood collected in EDTA (plot (a)).

EXAMPLE 1B

The analysis described in Example 1A was repeated for a number of different blood samples that were also measured on a commercial reference instrument (Beckman Coulter AcT5 hematology analyzer). FIGS. 12(a)-12(d) show the correlation between the results obtained by the apparatus and reagents of the present approach and those obtained by the reference instrument.

EXAMPLE 2

FIGS. 13(a)-13(e) show results from the same experiment as in Example 1, but using lytic reagents at pH 7.5, 6.1, 5.9, 5.3, and 4.6 respectively. In each case, 12.5 µL of whole blood collected in EDTA was mixed with 250 µL of the respective lytic reagent, incubated for about 30 seconds and run on the apparatus of the present approach. ALL, SSC and IALS were measured in each case and plotted pair-wise, as shown in FIGS. 13(a)-13(e). In each case, the leukocyte subpopulations were resolved in a manner similar to Example 1. Eosinophils were clearly differentiated from neutrophils by comparing ALL-vs-IALS signals and also by comparing IALS-vs-SSC signals. Lymphocytes, monocytes, basophils and granulocytes were identified by comparing ALL vs SCC. Basophils can be enumerated in each case in a similar manner as noted in Example 1.

EXAMPLE 3

FIG. 14 shows the ALL-vs-IALS light scatter plots for a blood samples exposed to the lytic reagent described in Example 1 above but whose pH were adjusted to be 7.5, 6.1, 8.9, and 5.9 respectively. In each case lymphocytes, monocytes, neutrophils and eosinophils were clearly resolved from one another. However, the position of the eosinophil population (highlighted by the dashed oval) relative to that of the neutrophil population (highlighted by the oval with a solid boundary) shifted noticeably along the ALL axis. In some case the eosinophils were above the neutrophils, in other cases it was below the neutrophils, and in some other cases it was at about the same level on the ALL axis as the neutrophils. This demonstrates that the ALL-vs-IALS detector configuration of the present approach was sensitive to subtle changes in cell sizes and reagent conditions. This property becomes important in measuring cell populations that differ only slightly from one another in size.

EXAMPLE 4

FIGS. 15(a)-15(e) show a IALS-vs-SSC light scatter plot for five different runs in which the pH of the lytic reagent was varied from acidic, to near neutral and to alkaline pH. In each case the resolution between the neutrophil and eosinophil population remained well defined. This positional relationship is important for at least three reasons: (i) this is the first time a 90° light scatter measurement has been used to consistently and reproducibly resolve eosinophils in human blood without using depolarizer or a fluorescent dye; (ii) the robustness of the IALS-vs-SSC as an analytical approach for identifying eosinophils under wider ranges of reagent conditions will allow one to explore various reagents for research as well as diagnostic assays without necessarily having to sacrifice this population in process of such measurement, and (iii) consistency is relative position improves the ability of an automated analytical software to more accurately discern the targeted populations. FIG. 15(f) summarizes the relative positions of the neutrophil and eosinophil positions for the five cases provided in this example to highlight the consistency and repeatability of their resolution.

EXAMPLE 5

In this example, a further subpopulation of a leukocyte subpopulation was resolved with an embodiment of the present approach and using only light scatter. In this embodiment the lytic reagent described in Example 1 was modified by additionally adding $MgCl_2$ in the formulation such that the ratio of $MgCl_2$ to NaCl was 1:4 in the final formulation. 250 µl of this modified lytic reagent was added to 12.5 µl of whole blood in EDTA, incubated for 30 seconds and run on the apparatus of the present approach. FIGS. 16(a) and 16(b) show the light scatter plot, comparing ALL-vs-SSC in FIG. 16(a), and IALS-vs-SSC in FIG. 16(b). As can be seen in FIG. 16(a), the lymphocyte population unexpectedly resolved into two populations, one with a low SSC (hereinafter called Lymph1) and the other with a higher SSC signal (hereinafter called Lymph2). As described in Example 6 below, the Lymph2 population was confirmed to be predominantly CD4 positive T-cells. FIG. 16(b) shows that eosinophils are resolved from neutrophils as in previous examples, thus demonstrating that in this case the reagent is specifically changing the lymphocyte subpopulation only.

EXAMPLE 6

In this example, in one embodiment, in addition to the ALL, SSC and IALS detectors, two fluorescence detectors were added, as described earlier in FIG. 7. Separately, 5 µl of PE labeled anti-CD3 and 5 µl FITC labeled CD4 antibodies were added to 40 µl of whole blood and incubated for 30 minutes. 12.5 µl of the antibody labeled sample is then mixed with 250 µl of the lytic reagent of Example 5 containing $MgCl_2$ as one of the ingredients, incubated for 30 seconds and run on the instrument described in this Example 6 that additionally included two fluorescence detectors capable of detecting fluorescence at about 520 nm and about 575 nm. Using a 488 nm laser, axial light loss, intermediate angle light scatter, side scatter, and fluorescence in two different wavelengths, 520 nm (±10 nm) and 575 nm (±10 nm) were measured for each cell as they passed though the interrogation zone of the flow cell. By gating on the cells that were both CD3 & CD4 positive on the fluorescence measurements FIG. 17(a), it was determined that the Lymph2 subpopulation on the ALL-vs-SSC light scatter plot (FIG. 17(b)) was primarily CD4 positive T-cells. Repeating the above experiment for five different human blood samples, the number of cells in the both CD3 & CD4 positive population were compared with the number of cells in the Lymph2 population, and plotted on a linear graph (FIG. 18). The linear correlation between the two measurements confirmed the identity of the second light scatter based lymphocyte subpopulation as being predominantly CD3 positive CD4 positive cells.

EXAMPLE 7

In this example about 7.75 µl of whole blood was added to about 2 ml of diluent. The diluent comprised about 20 µg/ml n-dodecyl-β-D-maltoside in phosphate buffered saline (PBS) at about pH 7.5 and about 290 mOsm. It should be appreciated that the diluent should be a non-lysing diluent, e.g., a diluent that does not lyse red blood cells. The sample was run in the instrument of the present approach and ALL and SSC signals were recorded and compared as shown in FIG. 19. Red blood cells and platelets were clearly differentiated from each other. On this figure, the population labeled as RBC doublets are red blood cells the come too close to each other in the interrogation zone of the flow cell and therefore their combined light scatter is measured as a single but larger electrical pulse. Each doublet event is therefore counted as two red blood cells in analysis.

In an embodiment of the instrument comprising additionally a fluorescence detector, immature red blood cells called reticulocytes can be identified by staining the RNA within the reticulocytes with a fluorescent dye, detecting the fluorescence, and identifying reticulocytes as depicted on FIG. 20.

As will be appreciated by one of skill in the art, aspects or portions of the present approach may be embodied as a method, system, and at least in part, on a computer readable medium. Accordingly, the present approach may take the form of a combination an apparatus, with or without reagents, and hardware and software embodiments (including firmware, resident software, micro-code, etc.), or an embodiment combining aspects of an apparatus with software and hardware aspects.

The terminology used herein is for the purpose of describing particular embodiments only and is not intended to be limiting of the approach. As used herein, the singular forms "a," "an," and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The present approach may be embodied in other specific forms without departing from the spirit or essential characteristics thereof. The present embodiments are therefore to be considered in all respects as illustrative and not restrictive, the scope of the present approach being indicated by the claims of the application rather than by the foregoing description, and all changes which come within the meaning and range of equivalency of the claims are therefore intended to be embraced therein.

I claim:

1. An apparatus for optically identifying and enumerating blood cells in a blood sample, the apparatus comprising:
    a container that contains at least one of a lytic reagent that lyses red blood cells and a diluent that does not lyse red blood cells;
    an optical flow cell;
    an energy source for emitting electromagnetic radiation in a first direction to illuminate a region of the flow channel;
    a light scatter detector array having no more than three light scatter detectors, the array having:
        a side scatter detector configured to measure light scatter around an axis substantially perpendicular to the first direction within a cone of full angle less than 50° centered around the axis,
        an intermediate angle light scatter detector, and
        one of an axial light loss detector and a forward light scatter detector;
    wherein the at least one of a lytic reagent that lyses the red blood cells and a diluent that does not lyse the red blood cells is a lytic reagent comprising a surfactant and an alkali metal salt in a hypotonic solution;
    wherein the lytic reagent comprises about 15 mM to about 30 mM of sodium chloride (NaCl), sodium dodecyl sulfate at a concentration of about 0.001% (w/v) to about 0.005% w/v, and is at a pH at about 7.0 to about 7.5; and
    wherein the intermediate angle light scatter detector is configured to detect light scattered at angles from about 25° to about 45° relative to the first direction.

2. The apparatus of claim 1, wherein identifying and enumerating blood cells comprises at least one of (a) the identification and enumeration of five subpopulations of leukocytes, and (b) the identification and enumeration of erythrocytes and thrombocytes.

3. The apparatus of claim 1, wherein the side scatter detector is configured to measure light scatter around an axis substantially perpendicular to the first direction within a cone of full angle of about 30° centered around the axis.

4. The apparatus of claim 1 wherein the intermediate angle light scatter detector is configured to detect light scattered within a polar angle from about 35° to about 45° and an azimuthal angle between 0° and about 90°, relative to the first direction.

5. The apparatus of claim 1 wherein the intermediate angle light scatter detector is configured to detect light scattered within a polar angle from about 35° to about 45° and an azimuthal angle between 20° and about 50°, relative to the first direction.

6. The apparatus of claim 1 wherein the intermediate angle light scatter detector is configured to detect light scattered within a polar angle from about 35° to about 45° and an azimuthal angle between 30° and about 35°, relative to the first direction.

7. The apparatus of claim 1, wherein the intermediate angle light scatter detector is configured to detect light scattered within a polar angle from about 41° to about 45° and an azimuthal angle between 0° and about 90°, relative to the first direction.

8. The apparatus of claim 1, wherein the intermediate angle light scatter detector is configured to detect light scattered within a polar angle from about 41° to about 45° and an azimuthal angle between 20° and about 50°, relative to the first direction.

9. The apparatus of claim 1, wherein the intermediate angle light scatter detector is configured to detect light scattered within a polar angle from about 41° to about 45° and an azimuthal angle between 30° and about 35°, relative to the first direction.

10. The apparatus of claim 1, wherein the one of an axial light loss detector and a forward light scatter detector is an axial light loss detector configured to measure electromagnetic radiation within an angle less than about 0.5° relative to the first direction.

11. The apparatus of claim 1, wherein the one of an axial light loss detector and a forward light scatter detector is a forward light scatter detector configured to measure light scattered at angles less than 3° but greater than about 0.5° relative to the first direction.

12. The apparatus of claim 1, wherein the lytic reagent includes at least one alkaline earth metal salt selected from the group consisting of magnesium halide, calcium halide, barium halide, and beryllium halide.

13. The apparatus of claim 1, wherein the lytic reagent comprises
 (a) a surfactant, and
 (b) an alkali metal salt selected from the group consisting of sodium halide and potassium halide;
 wherein the lytic reagent is maintained at an osmolality of the lytic reagent is between about 5 mOsm and about 150 mOsm.

14. The apparatus of claim 13, wherein the lytic reagent further comprises at least one alkaline earth metal salt selected from the group consisting of magnesium halide, calcium halide, barium halide and beryllium halide.

15. The apparatus of claim 1, further comprising a container with a non-lysing diluent.

16. The apparatus of claim 15, wherein the diluent comprises a non-ionic detergent.

17. The apparatus of claim 16, wherein the non-ionic detergent comprises n-dodecyl-p-D-maltoside.

18. The apparatus of claim 1, wherein the concentration of n-dodecyl-p-D-maltoside is adjusted to substantially sphere red blood cells when added to a whole blood sample.

19. The apparatus of claim 1, further comprising a fluorescence detector configured to detect fluorescent light emitted from the sample flowing through the flow channel.

20. A method for optically identifying and enumerating cells present in a blood sample, the method comprising:
 exposing at least one aliquot of the blood sample to at least one of a lytic reagent that lyses the red blood cells and a diluent that does not lyse the red blood cells;
 flowing a blood sample through a flow channel in an optical flow cell;
 focusing within the flow channel an electromagnetic radiation propagating in a first direction;
 detecting light scattered from cells flowing though the flow channel with a light scatter detector array having no more than three light scatter detectors, the array having:
 a side scatter detector,
 an intermediate angle light scatter detector, and
 one of an axial light loss detector and a forward light scatter detector;
 wherein the at least one of a lytic reagent that lyses the red blood cells and a diluent that does not lyse the red blood cells is a lytic reagent comprising a surfactant and an alkali metal salt in a hypotonic solution;
 wherein the lytic reagent comprises about 15 mM to about 30 mM of sodium chloride (NaCl), sodium dodecyl sulfate at a concentration of about 0.001% (w/v) to about 0.005% w/v, and is at a pH at about 7.0 to about 7.5; and
 wherein the intermediate angle light scatter detector is configured to detect light scattered at angles from about 25° to about 45° relative to the first direction.

21. The method of claim 20, wherein the at least one of a lytic reagent that lyses the red blood cells and a diluent that does not lyse the red blood cells is a diluent comprising a non-ionic detergent in a substantially isotonic solution.

22. The method of claim 20, wherein the lytic reagent further comprises at least one alkaline earth metal salt selected from the group consisting of magnesium halide, calcium halide, barium halide, and beryllium halide.

23. The method of claim 20, wherein the lytic reagent further comprises $MgCl_2$ and NaCl at the relative concentration ratio of about 4:1.

24. The method of claim 20, wherein the at least one of a lytic reagent that lyses the red blood cells and a diluent that does not lyse the red blood cells comprises a lytic reagent comprising an alkaline earth metal salt.

25. The method of claim 21, wherein the non-ionic detergent in the diluent is n-dodecyl-P-D-maltoside.

26. The method of claim 25, wherein the concentration of n-dodecyl-β-I)-maltoside in the diluent is adjusted to substantially sphere red blood cells when added to a whole blood sample.

27. A lytic reagent for selectively modifying the light scatter properties of at least one subpopulation of leukocytes, the lytic reagent comprising:
 a surfactant, an alkali metal salt, and an alkaline earth metal salt;
 wherein the lytic reagent is at a pH of about 4.5 to about 8.9, and the osmolality is maintained at about 5 mOsm to about 150 mOsm,
 wherein the alkaline metal salt is selected from the group consisting of sodium halide and potassium halide, and the alkaline earth metal salt is selected from the group consisting of magnesium halide, calcium halide, barium halide and beryllium halide, and
 wherein the ratio of the concentration of the alkali metal salt and the alkaline earth metal salt is 4:1.

* * * * *

UNITED STATES PATENT AND TRADEMARK OFFICE
CERTIFICATE OF CORRECTION

| | |
|---|---|
| PATENT NO. | : 10,215,683 B2 |
| APPLICATION NO. | : 15/767558 |
| DATED | : February 26, 2019 |
| INVENTOR(S) | : Chiranjit Deka |

Page 1 of 1

It is certified that error appears in the above-identified patent and that said Letters Patent is hereby corrected as shown below:

In the Claims

Column 23, Lines 10-12, please delete "of the lytic reagent is between about 5 mOsm and about 150 mOsm".

Column 23, Line 22, please change "-p-" to -- -β- --.

Column 23, Line 24, please change "-p-" to -- -β- --.

Column 24, Line 27, please change "-P-" to -- -β- --.

Column 24, Line 29, please change "-I-" to -- -D- --.

Signed and Sealed this
Sixteenth Day of April, 2019

Andrei Iancu
*Director of the United States Patent and Trademark Office*